United States Patent
Kazanchyan et al.

(10) Patent No.: US 10,172,757 B2
(45) Date of Patent: Jan. 8, 2019

(54) DEVICES, SYSTEMS, AND METHODS FOR MUSCLE RECOVERY

(71) Applicant: Hive Concepts, LLC, Fresno, CA (US)

(72) Inventors: Christofer Kazanchyan, Fresno, CA (US); Patrick Avakian, Fresno, CA (US); Victor Yaghoubi Mirzayan, Fresno, CA (US); Michael I. Fineberg, Chatsworth, CA (US); Martin Dalgaard, Chatsworth, CA (US); Kenneth A. Gross, Chatsworth, CA (US); Nikolas Francis, Chatsworth, CA (US); James Ibon, Chatsworth, CA (US); Giovanni Erick Guidetti, Altadena, CA (US); Robert Alan Berry, Fresno, CA (US)

(73) Assignee: Hive Concepts, LLC

( * ) Notice: Subject to any disclaimer, the term of this patent is extended or adjusted under 35 U.S.C. 154(b) by 0 days.

(21) Appl. No.: 15/154,690

(22) Filed: May 13, 2016

(65) Prior Publication Data

US 2016/0331620 A1    Nov. 17, 2016

Related U.S. Application Data

(60) Provisional application No. 62/324,881, filed on Apr. 19, 2016, provisional application No. 62/161,135, filed on May 13, 2015.

(51) Int. Cl.
*A61H 1/00* (2006.01)
*A61H 23/02* (2006.01)
(Continued)

(52) U.S. Cl.
CPC ............. *A61H 1/006* (2013.01); *A61H 11/00* (2013.01); *A61N 1/0452* (2013.01);
(Continued)

(58) Field of Classification Search
CPC ........ A61H 1/006; A61H 11/00; A61H 11/02; A61H 2011/005; A61H 2201/10;
(Continued)

(56) References Cited

U.S. PATENT DOCUMENTS 3,490,458 A   1/1970   Allison
4,175,551 A   11/1979  D'Haenens et al.
(Continued)

FOREIGN PATENT DOCUMENTS

EP        1 967 226       9/2008
WO    WO 2015/089383      6/2015
WO       2016183460 A1   11/2016

OTHER PUBLICATIONS

International Search Report and Written Opinion issued in PCT Application No. PCT/US2016/32400, dated Sep. 27, 2016, in 14 pages.

*Primary Examiner* — Rachel T Sippel

(57) ABSTRACT

A method, system and device for enhancing muscle training and performance by accelerating blood flow to the muscles and enhancing flow in the lymphatic system, incorporating mechanical stimulation and in some cases electrical stimulation of the muscle. A muscle recovery apparatus includes: an active compression device and an electrical stimulation device, where the active compression device is configured to be disposed about a user's muscle and to mechanically compress the user's muscle to facilitate muscle recovery, and where the electrical stimulation device is coupled to an inner surface of the active compression device, such that the electrical stimulation device can be placed in contact with the user to electrically stimulate the user's muscle.

26 Claims, 17 Drawing Sheets

(51) Int. Cl.
*A61N 1/36* (2006.01)
*A61N 1/04* (2006.01)
*A61H 11/00* (2006.01)
*A61F 7/00* (2006.01)

(52) U.S. Cl.
CPC ......... *A61N 1/0456* (2013.01); *A61N 1/0484* (2013.01); *A61N 1/36003* (2013.01); *A61N 1/36014* (2013.01); *A61F 7/007* (2013.01); *A61F 2007/0071* (2013.01); *A61F 2007/0075* (2013.01); *A61H 23/0218* (2013.01); *A61H 2011/005* (2013.01); *A61H 2201/0207* (2013.01); *A61H 2201/0214* (2013.01); *A61H 2201/0228* (2013.01); *A61H 2201/0257* (2013.01); *A61H 2201/0285* (2013.01); *A61H 2201/10* (2013.01); *A61H 2201/1207* (2013.01); *A61H 2201/1215* (2013.01); *A61H 2201/1436* (2013.01); *A61H 2201/164* (2013.01); *A61H 2201/165* (2013.01); *A61H 2201/1614* (2013.01); *A61H 2201/5007* (2013.01); *A61H 2201/5038* (2013.01); *A61H 2201/5043* (2013.01); *A61H 2201/5048* (2013.01); *A61H 2201/5082* (2013.01); *A61H 2205/10* (2013.01); *A61H 2205/106* (2013.01); *A61H 2209/00* (2013.01); *A61H 2230/06* (2013.01); *A61H 2230/207* (2013.01); *A61H 2230/30* (2013.01); *A61H 2230/50* (2013.01); *A61H 2230/65* (2013.01)

(58) Field of Classification Search
CPC ...... A61H 2201/1215; A61H 2201/165; A61H 2209/00; A61N 1/0452; A61N 1/36003; A61N 1/36014
See application file for complete search history.

(56) References Cited

U.S. PATENT DOCUMENTS

| | | | |
|---|---|---|---|
| 5,010,896 A | 4/1991 | Westbrook | |
| 5,397,338 A | 3/1995 | Grey et al. | |
| 5,674,262 A | 10/1997 | Tumey | |
| 5,766,236 A | 6/1998 | Detty et al. | |
| 6,132,392 A | 10/2000 | Stone | |
| 6,213,960 B1 | 1/2001 | Sherman et al. | |
| 6,829,510 B2 | 12/2004 | Nathan et al. | |
| 7,011,637 B2 | 3/2006 | Sherman et al. | |
| 7,445,608 B2 | 11/2008 | Dunfee et al. | |
| 7,497,837 B2 | 3/2009 | Sherman et al. | |
| 7,637,879 B2 | 12/2009 | Barak et al. | |
| 7,991,476 B2 | 8/2011 | Nachum | |
| 8,209,030 B2 | 6/2012 | Minogue et al. | |
| 8,265,763 B2 | 9/2012 | Fahey | |
| 8,285,381 B2 | 10/2012 | Fahey | |
| 8,308,665 B2 | 11/2012 | Harry et al. | |
| 8,388,557 B2 * | 3/2013 | Moomiaie-Qajar | A61H 11/00 128/882 |
| 8,579,841 B2 | 11/2013 | Khan | |
| 8,753,299 B1 * | 6/2014 | Waldon, Sr. | A61H 23/02 601/46 |
| 8,755,894 B2 | 6/2014 | Nachum et al. | |
| 8,892,210 B2 | 11/2014 | Fahey | |
| 9,302,104 B2 | 4/2016 | Fahey | |
| 2002/0151951 A1 | 10/2002 | Axelgaard et al. | |
| 2003/0114892 A1 | 6/2003 | Roger et al. | |
| 2004/0030270 A1 | 2/2004 | Johnson | |
| 2004/0254624 A1 | 12/2004 | Johnson | |
| 2007/0100214 A1 * | 5/2007 | Steinert | A61H 1/00 600/300 |
| 2007/0173886 A1 * | 7/2007 | Rousso | A61H 7/001 606/203 |
| 2008/0071202 A1 | 3/2008 | Nardi | |
| 2010/0056966 A1 | 3/2010 | Toth | |
| 2010/0057149 A1 * | 3/2010 | Fahey | A61H 11/00 607/3 |
| 2010/0198115 A1 | 8/2010 | Koeneman et al. | |
| 2011/0082517 A1 | 4/2011 | Brezel et al. | |
| 2011/0093035 A1 * | 4/2011 | Moser | A61N 1/0456 607/48 |
| 2012/0172940 A1 | 7/2012 | Wahls et al. | |
| 2012/0238924 A1 | 9/2012 | Avni | |
| 2013/0085420 A1 | 4/2013 | Feinstein | |
| 2014/0052030 A1 * | 2/2014 | Shields | A61H 1/006 601/15 |
| 2014/0088476 A1 * | 3/2014 | Logan | A61H 9/0078 601/152 |
| 2014/0213940 A1 | 7/2014 | Mayer | |
| 2014/0276257 A1 | 9/2014 | Santa Maria et al. | |
| 2015/0032038 A1 * | 1/2015 | Atry | A61H 7/001 601/84 |
| 2015/0224011 A1 | 8/2015 | Scott et al. | |
| 2015/0297909 A1 | 10/2015 | Peashock | |

* cited by examiner

DEVICES, SYSTEMS, AND METHODS FOR MUSCLE RECOVERY

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application is a non-provisional application which claims benefit of priority to U.S. Provisional Patent Application Ser. No. 62/161,135, filed on May 13, 2015, and U.S. Provisional Patent Application Ser. No. 62/324,881, filed on Apr. 19, 2016, both of which are incorporated herein by reference in their entireties.

BACKGROUND OF THE INVENTION

Field of the Invention

This application is directed to devices, systems, and methods for enhancing training and performance of tissues, such as for example muscles, by accelerating muscle recovery and reducing the time needed for muscles to recover. The application of pressure, such as for example, compression, of muscle tissue can be provided in a continuous, fluctuating or rapidly fluctuating mode in various combinations with one or more additional muscle recovery modalities.

Description of the Related Art

There are four main factors that regulate muscle recovery in adequately hydrated, nourished and rested individuals. They include availability of nourishment elements, timely and effective removal of waste from the muscles, production and release of myokines, and remodeling of the repaired tissue.

These goals are achieved via active muscle recovery as it drives the four processes previously mentioned. As skeletal muscles are activated, they send a message to the smooth muscles that surround the blood vessels to relax. Consequently, the blood vessels dilate and circulation increases. Further factor in recovery is the lymphatic system's ability to remove waste byproducts created via the lymphatic drainage. Understanding that the lymphatic system is passive, the movement of waste through the lymphatic system is dependent upon the activation of the muscles that surround the lymphatic vessels. Therefore muscle activation is needed to push waste through the complex lymphatic system. Additionally, muscle activation provides the needed mechanical stress to induce the production and release of myokines involved in aiding the muscle tissue regeneration process. Finally, repaired muscle tissue requires mechanical stress to optimally remodel into healthy form and function. Without active recovery's mechanical stress un-repaired, unhealthy, and dysfunctional movement may result.

Light exercise including walking, cycling, swimming in traditional active recovery can be very helpful. However, it is limited and can be a negative as well. If the recovery activity is too long, aggressive, or incorrectly oriented further fatigue and stress will be created rather than positive recovery. Also, inadequate amounts or levels will not attain desired levels of recovery. Finally, there is the psychological factor of having to return to the environment associated with the difficult training session which created the fatigue to begin with.

Muscle pain, tenderness and fatigue experienced after various levels of exercise are primarily due to muscle cell micro damage and inflammation. This damage and inflammation leads to the accumulation of metabolic waste products which the body cannot clear completely during exercise or normal cool down. As the muscles continue to work, increasing accumulation of waste in the muscle leads to a decrease in performance and more muscle fatigue. In order to recover the muscle and rid the body of these waste products, these waste products must be removed via the venous and lymphatic system. The lymphatic system and blood vessels work together to flush waste products from our cells naturally. Muscular movement, however, is needed to stimulate this process because the lymphatic system is not able to create its own pressure gradient to induce flow. In this regard the lymphatic system is unlike the cardiovascular system, where the heart creates a pressure gradient by its pumping function. Often times, the promotion of removing waste is accomplished by light muscle movements, to achieve muscle contraction and increase circulation in the body, thereby reducing soreness in the muscles. Although the human body naturally excises waste that causes soreness and fatigue, this takes time, and also produces additional waste product from the lightly exercised muscles.

SUMMARY OF THE INVENTION

Consequently, technology to improve active recovery, creates a highly control-able and customizable experience and environment allowing for: muscle activation to increase availability of nourishment via blood flow, increase removal of waste via lymphatic drainage, produce sufficient myokines by maximizing muscle fiber recruitment, and create mechanical stresses needed to encourage repair and remodeling without causing additional fatiguing. Additional advantages include recovery that is accelerated, enjoyable, and offers improvement of the vascular system's capability for future usage.

In one embodiment, a muscle recovery apparatus includes: an active compression device and an electrical stimulation device, where the active compression device is configured to be disposed about a user's muscle and to mechanically compress the user's muscle to facilitate muscle recovery, and where the electric simulation device is coupled to an inner surface of the active compression device, such that the electrical stimulation device can be placed in contact with the user to electrically stimulate the user's muscle.

The muscle recovery apparatus may be configured to attach and communicate with one or more additional muscle recovery apparatuses, to accommodate larger muscles.

One or more muscle recovery apparatuses may be pivotally attached to one another to allow for relative movement in at least one axis.

Compression of the muscle and stimulation of the muscle may be sequenced, and configured to activate medial to the user's heart.

The muscle recovery device may further include a thermal manipulation device to manipulate perfusion in the user's muscle.

The muscle recovery device may further include a vibrator.

The active compression device may be removably fitted and adjusted upon the muscle by a fastening means.

The muscle recovery device may further include a control module in communication with the active compression device and the electrical stimulation device.

The control module may be configured to adjustably and independently control active compression and electrical stimulation of the user's muscle.

Control of active compression and electrical stimulation by the control module may be configured to implement a rhythmic pattern.

The active compression device may include: a motor mounted on a housing at a rotational shaft of the motor, and a strap removably attached to the motor, such that rotating the motor in one direction retracts the strap, and rotating the motor in an opposite direction unwinds the strap.

The electrical stimulation device may include: a power source, and at least two electrode pads in electronic communication with the power source.

The power source may include at least one of: a battery, an AC supply, a DC supply, and a photovoltaic supply.

The active compression device may include: a motor mounted on a housing, a cord affixed to a rotating shaft of the motor, and at least one pulley configured to receive the cord, where rotating the motor in one direction retracts the cord, increasing compression, and where rotating the motor in an opposite direction unwinds the cord, relieving compression.

The muscle recovery device may further include at least one sensor for monitoring biometrics of the user.

The active compression device may be configured to be disposed entirely around the user's muscle.

The active compression device may be configured to facilitate blood flow and the electrical stimulation may be configured to electrically stimulate the user's muscle to mimic muscle contraction.

In another embodiment, a muscle recovery apparatus includes an active compression device, and an electrical stimulation device, where the active compression device is configured to surround a user's muscle and to mechanically compress the user's muscle to facilitate blood flow, where the electrical stimulation device is disposed on the muscle recovery device to be placed in contact with the user, and when so placed, electrically stimulate the user's muscle to mimic muscle contraction, and the active compression device is configured to be removably coupled atop the electrical stimulation device.

The electrical stimulation device may be removably affixed to the user by a fastener.

The active compression device may be removably coupled atop the electrical stimulation device by a fastener.

The fastener for affixing the electrical stimulation device to the user may include at least one of: a strap, resilient fabric, mesh, wires.

In another embodiment, a method for treating a muscle includes: affixing an electrical stimulation device on a user, affixing an active compression device on a user, enacting the electrical stimulation device to electrically stimulate the muscle, and enacting the active compression device to mechanically compress the muscle.

The method for treating a muscle may further include synchronizing enactment of the electrical stimulation device and the active compression device, to treat the muscle.

The method for treating a muscle may further include independently adjusting the electrical stimulation device and the active compression device to adjust the electrical stimulation and mechanical compression to the desired specification.

The method for treating a muscle may further include coordinating enactment of the electrical stimulation device and the active compression device in a sequential manner.

The method for treating a muscle may further include coordinating enactment of the electrical stimulation device and the active compression device in a non-sequential manner.

In another embodiment, a muscle recovery device includes a motor mounted on a housing at a rotational shaft of the motor; and a strap removably attached to the motor, such that rotating the motor in one direction retracts the strap, and rotating the motor in an opposite direction unwinds the strap.

BRIEF DESCRIPTION OF THE DRAWINGS

These and other features, aspects and advantages are described below with reference to the drawings, which are intended to illustrate but not to limit the inventions. In the drawings, like reference characters denote corresponding features consistently throughout similar embodiments. The following is a brief description of each of the drawings.

DETAILED DESCRIPTION

Figure 1:
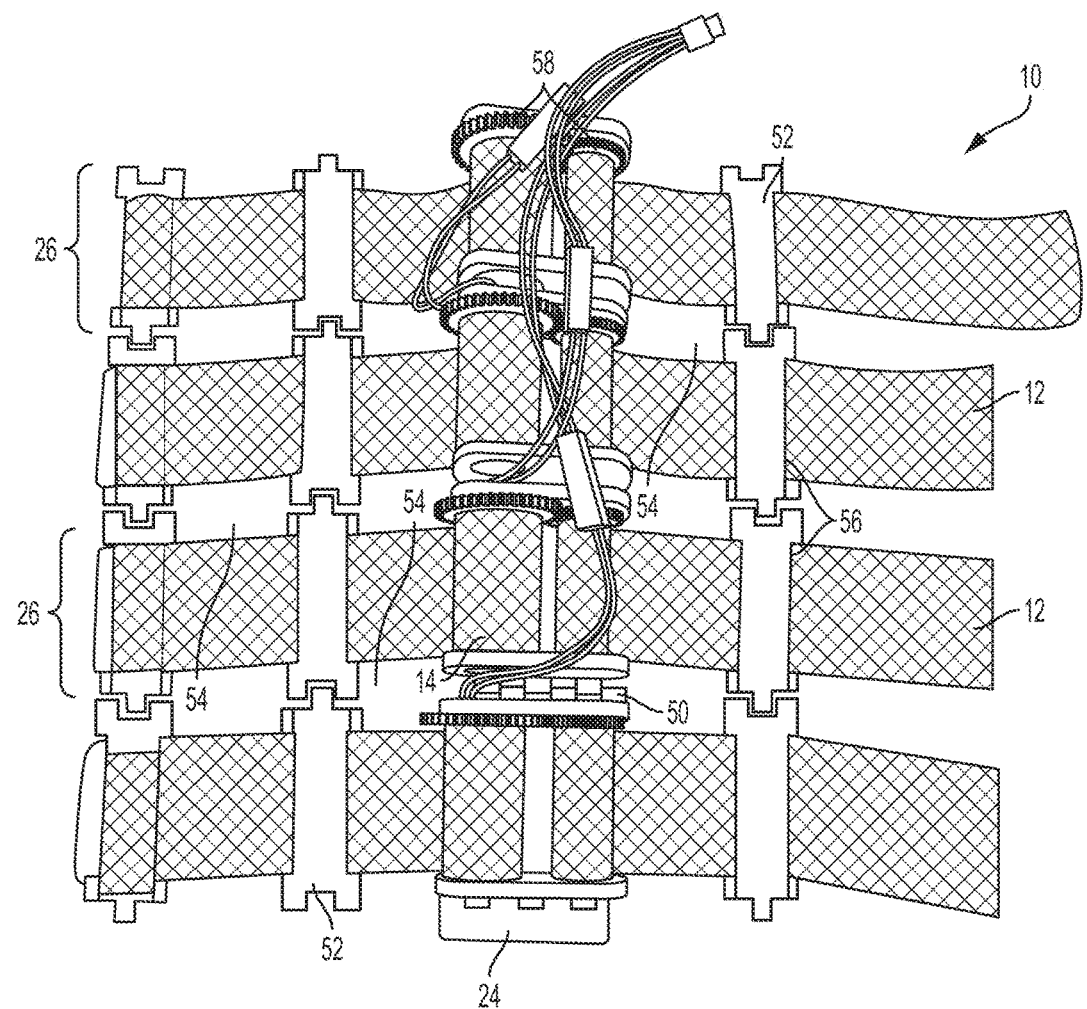
FIG. 1 depicts a front perspective view of an example embodiment.
Figure 2:
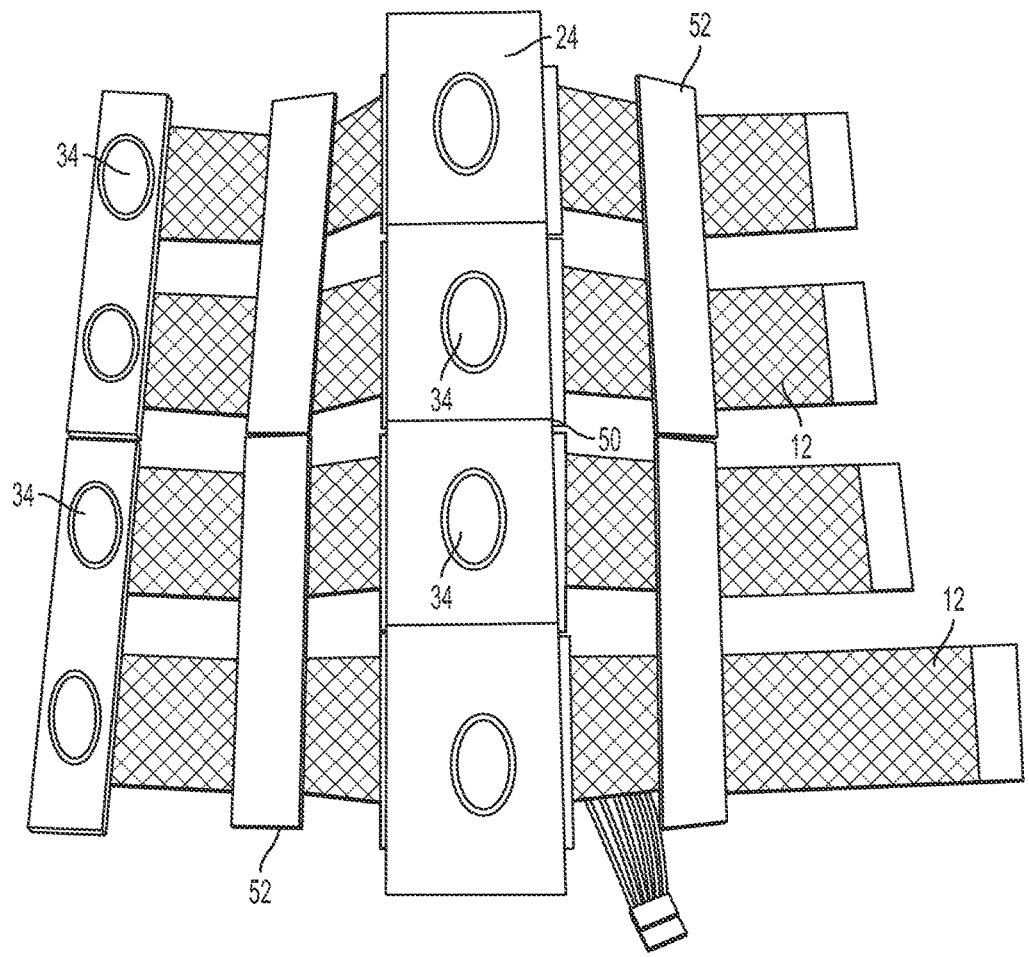
FIG. 2 illustrates a rear perspective view of an example embodiment.

As discussed above, this disclosure is directed to hastening recovery and enhancing performance of muscles. This technology is well suited to modulating the recovery part of training. Athletic training results in muscle breakdown, which is followed by a recovery period. The recovery period can be shortened and muscle rebuilding enhanced by any one of, or a variable combination of: affecting the blood flow to the muscles; affecting the lymphatic system; affecting local tissue and core body temperatures; increasing amount of muscle fiber recruitment with associated regulatory component molecules; and/or affecting the psychological state with associated regulatory component molecules.

These effects can be modulated in a controlled manner by using mechanical or physical compression of muscles alone or in combination with electrical muscle stimulation and/or temperature regulation. Furthermore, segmental zones utilizing a combination of biological recovery processes can create a customizable, sequential (or non-sequential), and rhythmic recovery experience synergistically influenced by desired environmental components. The compression aspect may be accomplished by peristaltic compression, sequenced compression, isolated compression, random compression and/or combinations therefrom. The potential value of various embodiments herein can arise from muscle recovery and rejuvenation from fatigue, muscle rehabilitation from injury, pain management, or even entertainment.

Without being bound to any specific theory, the recovery model can be viewed from three perspectives: pain management, efficacy with depth of tissue recruitment, and a psychological (or placebo) component. First, pain management can deal with the gate control theory model which allows one type of sensory nerve stimulation at a peripheral location to block another type of nerve stimulation from reaching conscious awareness in the brain. Thus varying the types and timing of nerve stimulation, including sharp and dull stimuli, creates an altered perception of sensations with pain, for example. Second, varying depths of tissue penetration can be achieved based on the type and strength of modality used. The embodiments disclosed herein can provide one or a combination of modalities including massage compression with outer surface to deep tissue, vibration with radiating wave component throughout the tissue, and Transcutaneous Electrical Nerve Stimulation (hereafter referred to as "TENS") with multiple potential levels of tissue involvement based on electrical components. The specific level of tissue recruitment is a function of the type and strength of the modality used. The psychological role is significant in accelerating the engagement of the parasympathetic nervous system into action from the previous sympathetic nervous system involved with muscle exertion. The parasympathetic nervous system's activation can play an important role in enhanced tissue recovery. The combination of these three perspectives in the recovery model plays an important role in enhancing and even optimizing speed and effectiveness. Furthermore, they synergistically enable increased mobility of the individual post modality usage thereby continuing the natural recovery process afterwards.

External compression has been a method used for muscle recovery, primarily by pushing waste out of the treated limbs. However, too much pressure (such as for example, by use of a tourniquet) can essentially stop blood circulation thereby halting the recovery effort, and too little pressure contributes essentially nothing to the recovery effort. Additionally, squeezing the skin does not activate muscles, which is the key factor in pushing waste through the complex network of lymphatic vessels. Although the benefits of compression are advantageous to recovery, during external compression (such as, for example, squeezing the skin), blood flow is significantly reduced, which hinders blood flow.

An additional method for lightly exercising muscles without producing fatigue and waste is accomplished using electrical stimulation of the muscle. Electrical stimulation involves stimulating nerves and skeletal muscle. The stimulation affects motor neurons, which innervate or stimulate skeletal muscle fibers. The electrical stimulus contracts the muscle, which may be controlled in various patterns/timeframes detailed below. The electrical stimulus may produce quick contractions, contractions with pauses between contractions, or contractions that are held for specific lengths of time, for example. These contraction types result in improved warming up, strength, and recovery of the muscles.

The electrical stimulus may be delivered to the muscles via electric probes placed on pads, and applied directly to the skin at various ends, or on multiple sites of the skeletal muscle to be stimulated. A varied amount of current may be delivered to the muscle, wherein the adjustability allows for adaptation to larger and smaller muscles, as well as comfort levels of various individuals. The current runs at varied frequencies (Hz) and pulse durations (microseconds). The motor neurons found within the area are stimulated. The muscle fibers innervated by the motor neurons then contract.

Changing frequencies can change which kinds of muscle fibers are being stimulated. For example, three ranges of frequencies stimulate three kinds of motor neurons-muscle fiber types. A slow twitch muscle fiber will contract at one set of frequencies while an intermediate fast twitch muscle fiber will contract at a different set of frequencies. Likewise, fast twitch muscle fiber has its own set of frequencies that it reacts to.

Figure 5:
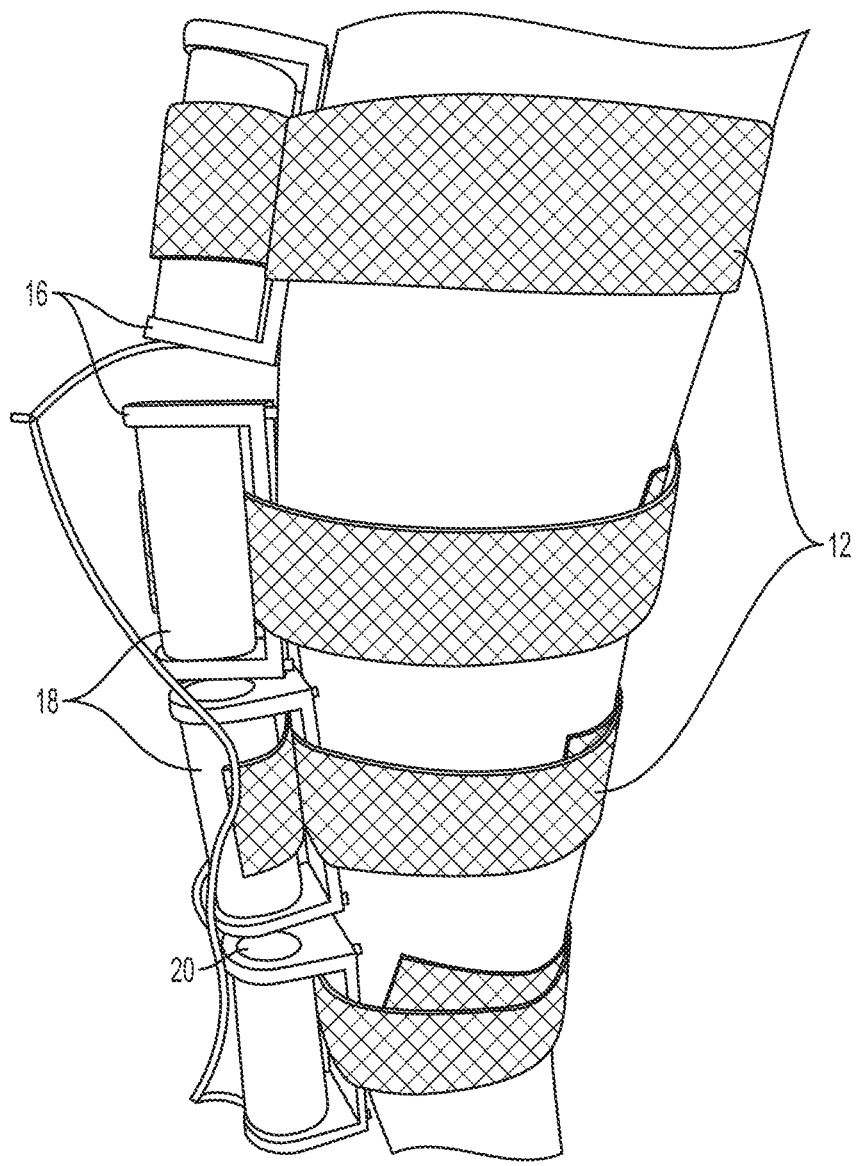
FIG. 5 depicts a side perspective view of an example embodiment.
Figure 6:
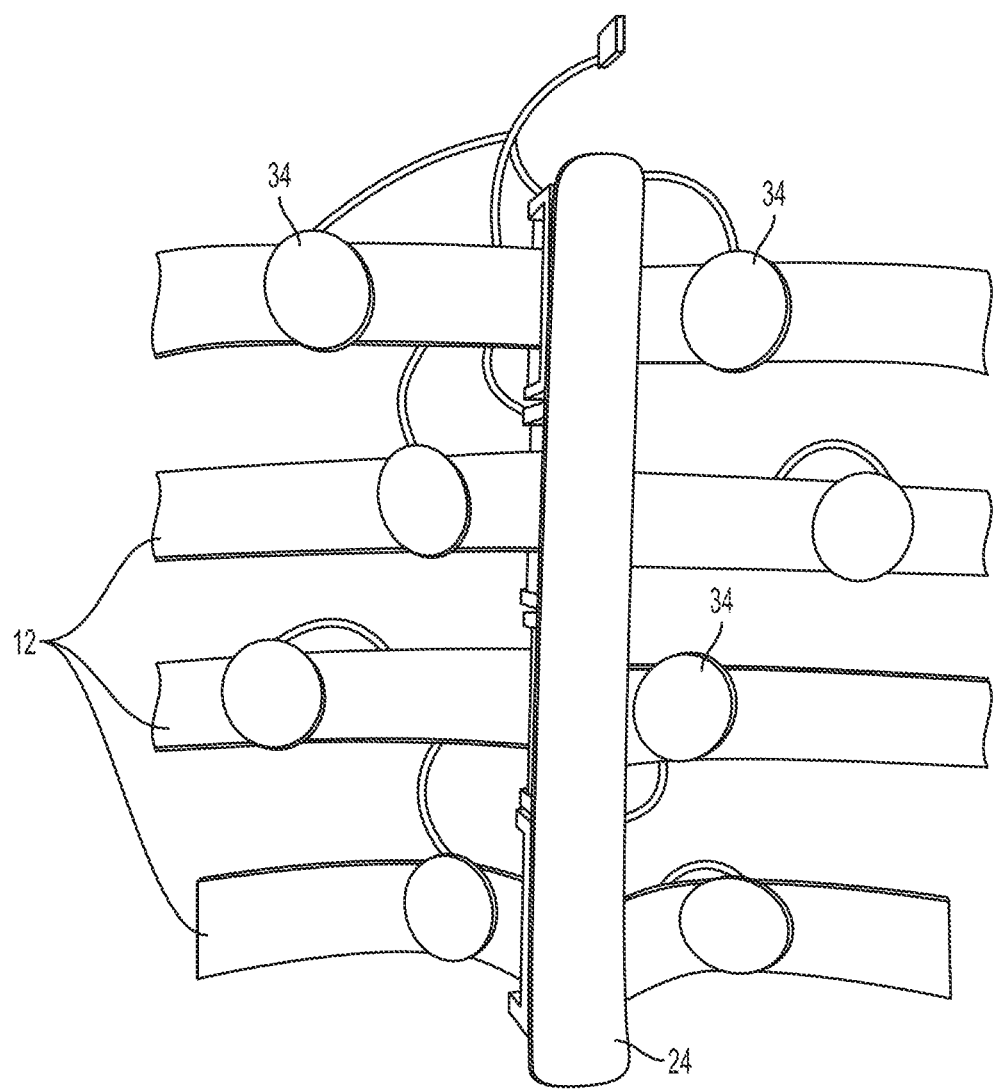
FIG. 6 depicts a rear perspective view of an example embodiment.

Embodiments described herein provide a combination of mechanical and electrical stimulation to an end user's muscle for rapid muscle recovery by removing waste, and relaxing the muscle for quick recovery. In one embodiment, shown in FIGS. 5 and 6, the stimulation is applied to the user's leg to stimulate blood flow. The device 10 is attached to the leg by a series of hook and loop straps 12 that go around the leg and connect on the far side. A motor 14 is mounted and mechanically attached to each of the straps 12. Each motor 14 is mounted inside a housing 16 which includes a large barrel 18 attached to the rotating shaft 20 of the motor 14. The housing 16 encapsulates the entire motor 14. The motor 14 is mounted to the base 24 of the device 10. The exterior barrel 18 is connected to the shaft 20 of the motor 14. The shaft 20 and the barrel 18 can spin relative to the base 24 when the motor 14 is activated. One end of the strap 12 is attached to the base 24 of the device 10 and the other is mounted to the exterior barrel 18 (not shown in FIG. 4). When the motor 14 is activated, the barrel 18 rotates and begins to draw in the strap 12 connected to it. The strap 12 goes around the leg and is connected to the base 24 of the motor 14. The connection between the strap 12 and the motor can be any suitable connection device, such as a hook and loop connection, snaps, clasps. This allows for the device 10 to deliver a compressive force to the leg when the motor 14 is activated.

By attaching multiple devices 10, each with its own motor 14 and strap 12, a wrap is created around the muscle with multiple segments 26. A segment 26 can be a unit including one motor 14 and one strap 12, as well as one or a plurality of connectors that enable multiple modular segments 26 to be connected to and/or disconnected from each other. The segments 26 may be attached to one another using one or more of a variety of connectors, including, for example, snap connectors, zippers, or the like. The motor 14 of each segment 26 can be individually activated to provide a sequential compression of any pattern desired. The motors 14 will be driven by a control unit 28 which will control the power allocation to activate the motors 14. A microprocessor 30, in communication with the control unit 28, will control the activation, allowing for various patterns and adjustability. The user will be able to communicate to the unit via USB, Bluetooth, or other wired or wireless means. This allows for user control during use from one or more inputs that are external to the device 10, such as for example, on-the-fly adjustability. Various motor 14 activation schemes may be implemented. For example, to reduce power consumption or to apply less pressure, the motors 14 can be pulse-width modulation (PWM) activated. Another possible motor activation scheme would be to pulse activate the motors 14 instead of a linear activation. This would be similar to PWM activationing, except the duty cycle would remain at about 50% and only the frequency would be altered. In one example, a pulse frequency of about 15 Hz is provided, with the option to increase or decrease the frequency at the user's discretion. Furthermore, adding a slight reverse of the motors after engagement has ended to help loosen the straps would exaggerate the next compression. In some embodiments, a stepper motor may be used. In other embodiments, a solenoid may be used to control the active compression.

In various embodiments, the straps 12 may incorporate a two part strip of heavy cloth (or other material which might include, for example, Lycra® or E.V.A. foam) to wrap around the leg, a first part of the strip may incorporate one or more TENS electrodes placed on the inside of the strip, both parts of the strip are held together with an elastic band. The motor 14 and remaining components sit on the outside of said cloth. Each horizontal segment 26 has its own cloth undercarriage containing all the components necessary for function. Segments 26 may be attached to one another horizontally (for example, by zippers or Velcro®) to form a seamless undercarriage to hold the entire device 10 together. Lycra®or other elastic material may be used between each segment 26, attached between the zipper and strap 12, allowing for flexibility in the device 10 to conform to the shape and contour of diverse regions of the body. The undercarriage fabric may be of an optically clear material so that the user can see where the pads are being placed. Additionally, an embodiment can incorporate various materials (attached or removable) which can be heated or cooled prior to use, and in some cases, stored in a temperature controlled format (hot or cold). This initial application along with continued application during use of the device 10 aids in user's desired temperature modification of local and core tissues to benefit recovery efforts.

To keep the unit from moving during use, a sequence to force the entire device 10 to constantly snake/inch up or down the muscle can be implemented. The control unit 28 may also control the electrical stimulation. The electrical stimulation may be a high voltage of about 170V, a low current of about 180µA with a bipolar pulse lasting about 7 ms. The pulse may be delivered to the user's muscle via a conductive pad or fabric attached to the inside of the segment 26 used for mechanical compression. The conductive pad will make a low impedance contact with the user's skin for an efficient delivery of the electrical stimulation to the target muscle. Each segment 26 can have its own set of conductive pads which can be placed diametrically opposed to one another. Each set of electrodes will also be electrically isolated to negate cross activation of unwanted electrodes. The user may control the amplitude of the pulse to a desired level on the fly through the microprocessor 30 or another micro-controller. The frequency can be set to be in synch with the mechanical activation or it may be changeable by the user.

The activation sequence encourages fluid flow towards the heart. This is accomplished by sequentially activating segments 26, both mechanically and electrically, beginning from a position most distal to the strap 12, and concluding at a position closest to the heart. The particular activation scheme may be user settable. In one example, to the activation scheme engages the bottom most of the activating segments 26 electrically and mechanically at the same time, holding the mechanical compression, while providing a single electrical pulse to that particular segment 26. The activating segments 26 immediately above may be activated next. As in the previous step, the electrical activation may be a pulse while the mechanical activation may be to hold the compression. As soon as the mechanical activation has reached its peak compression, the mechanical compression of the strap 12 below the previous position is deactivated, and the next strap 12 above is activated. This sequence continues all the way to the top, and then the sequence begins again from the bottom. There may be a pause installed between finishing one cycle and beginning a new cycle, or if the user desires, the next cycle can be initiated before the last one completes. All the sequencing schemes may be user adjustable.

Figure 3:
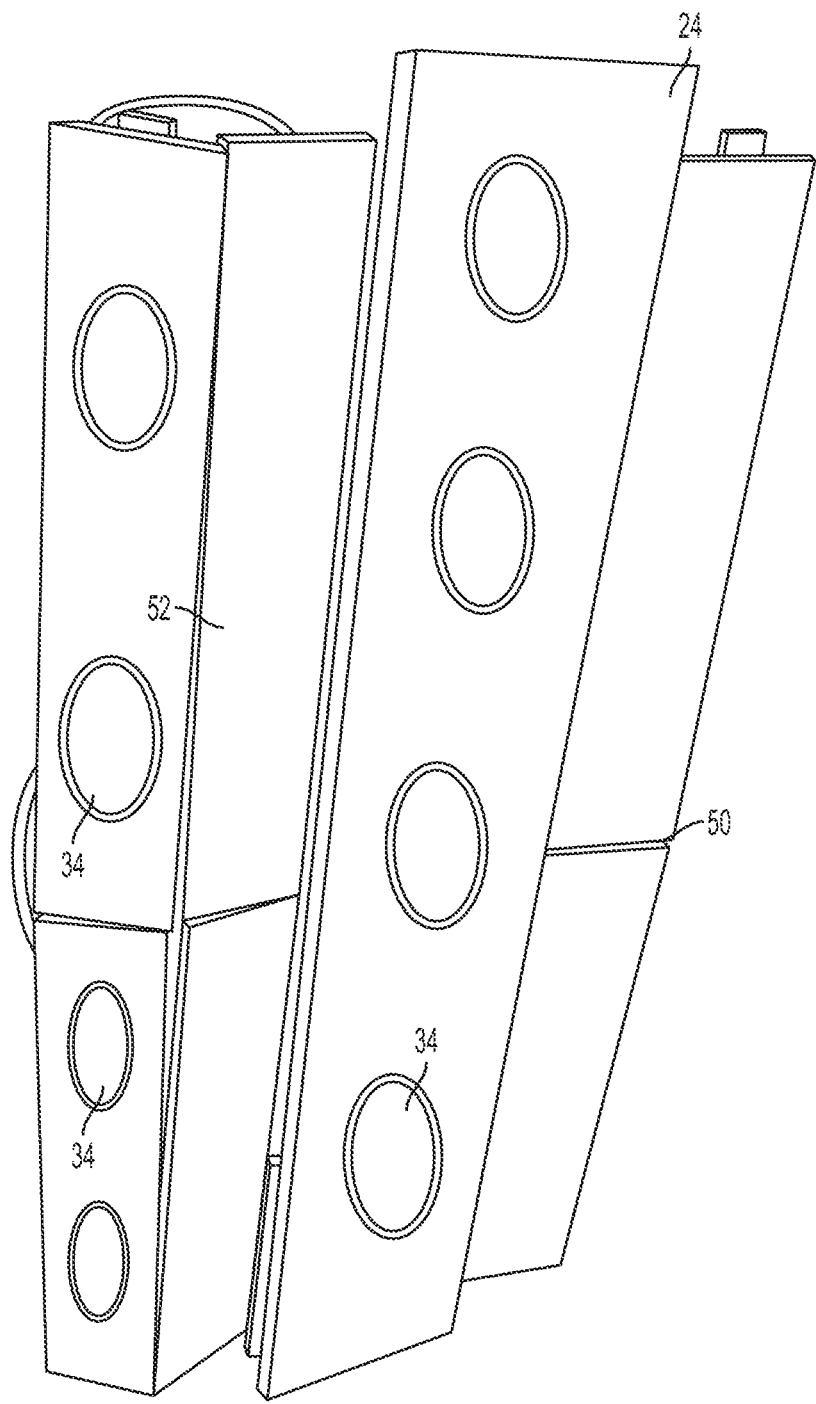
FIG. 3 depicts a rear perspective view of an example embodiment.
Figure 4:
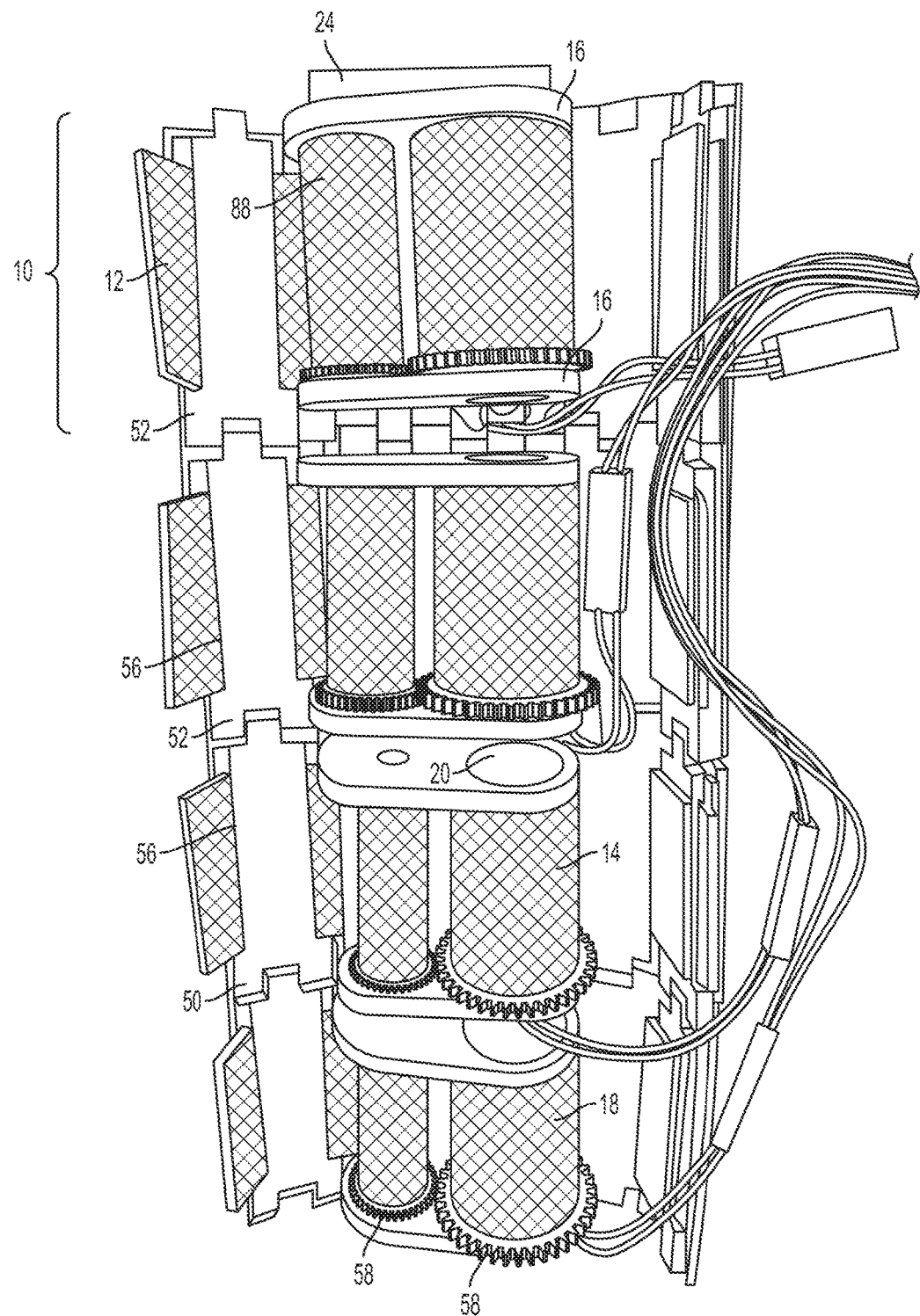
FIG. 4 provides a front perspective view of an example embodiment.

In an embodiment depicted in FIGS. 1-4, the motors 14 and other components may be situated on a flexible mechanical link 50 between the base 24 of the housing 16 of each motor 14. This positioning eliminates the need for a cloth undercarriage. The straps 12 may be made to wind in on both sides such that the device 10 provides a more even compression. Also, the straps 12 may wind up completely, as depicted in FIGS. 3 and 4, thereby resulting in a more compact and portable device. The TENS electrodes, which can be a part of or coupled with the electrode pad 34 may be placed below the motors 14 and/or at the end of the straps 12. This would allow for the TENS electrodes to be placed up to 180 degrees apart from one another, and for the device 10 to conform to a wide range of limb sizes. There are gaps 54 between each interconnected device 10. A mechanism that fastens the straps 12 (such as, for example, a zipper) of adjacent horizontal segments 26 together as they are ejected from the motors 14 may be used to address the gaps 54. To keep the straps 12 evenly spaced, multiple vertical rods 52 can be used. The vertical rods 52 may have slots 56 with adequate spacing to accommodate the straps 12 to slide therethrough. The rods 52 provide for continuous compression as the segments 26 are sequentially activated. Allowing the straps 12 to slide through the vertical rods 52 also reduces chafing on the user's skin. Additionally, the underneath area of these vertical rods 52 could include rollers (not shown) against the skin to aid in trigger point associated massage compression while also balancing out high and low pressure points for more ideal circumferential uniformity. The base 24 may include a stiff, or semi-stiff plastic molded to the shape of the limb to provide a more stable base for all the components to attach to.

In some embodiments, two motors 14 each with its respective barrel 18, oriented in opposite directions, can be used to enable pull from two directions. This two-directional pull allows for a more even compression. This two-directional pull may also be accomplished by using one motor 14, as depicted in FIGS. 1-4, and by mechanically coupling the second barrel 88 through spur gears 58. In some embodiments, a single motor 14 and single barrel 18 can be employed by attaching both straps 12 onto opposite sides of the barrel 18, about 180 degrees apart. The single motor, single barrel configuration may provide some stress on the barrel 18, but one of the straps 12 is attached to the top of the barrel 18, causing the mounting to torque into the user's body, and some of the stress can be reduced by redirecting the top strap 12 through a slot close to the base 24 of the mount and at the same level as the opposing strap.

Figure 13:
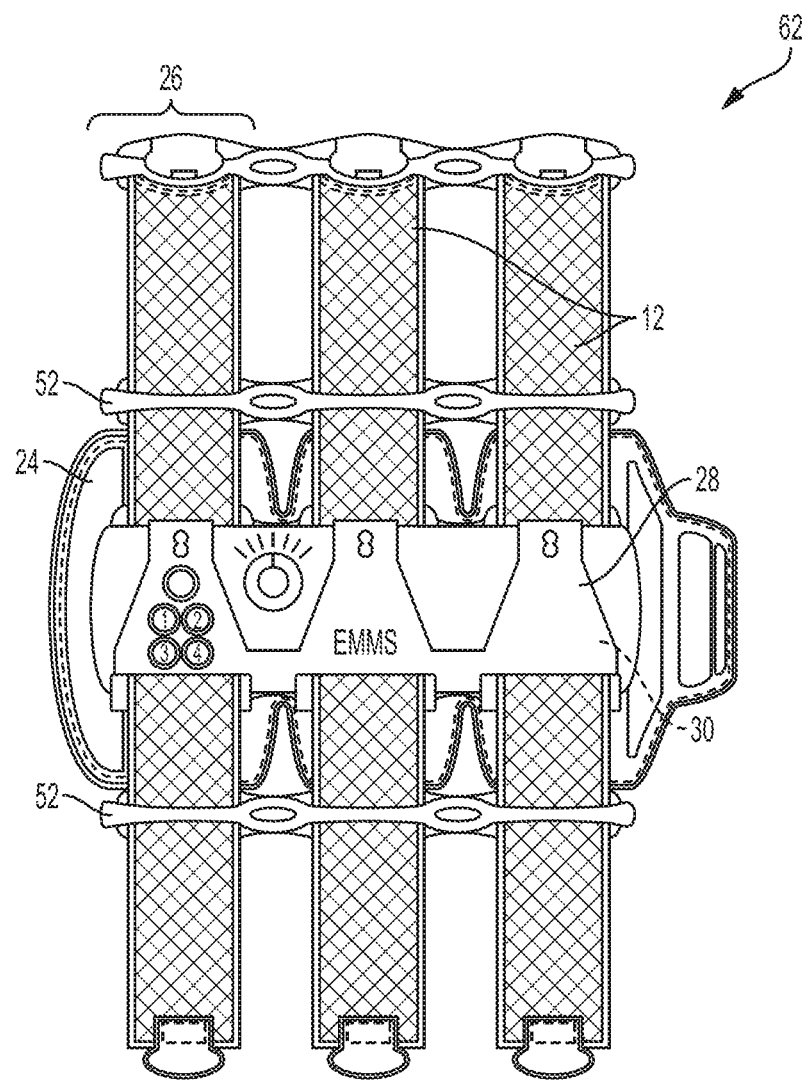
FIG. 13 depicts a front perspective view of an example embodiment.
Figure 14A:
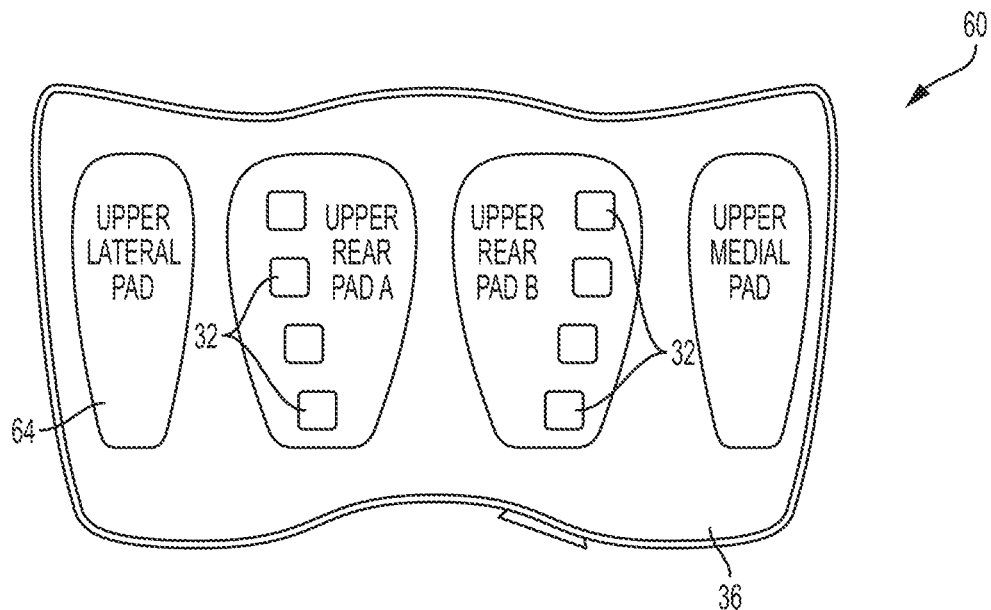
FIGS. 14A-B provide planar perspective views of an example embodiment.
Figure 14B:
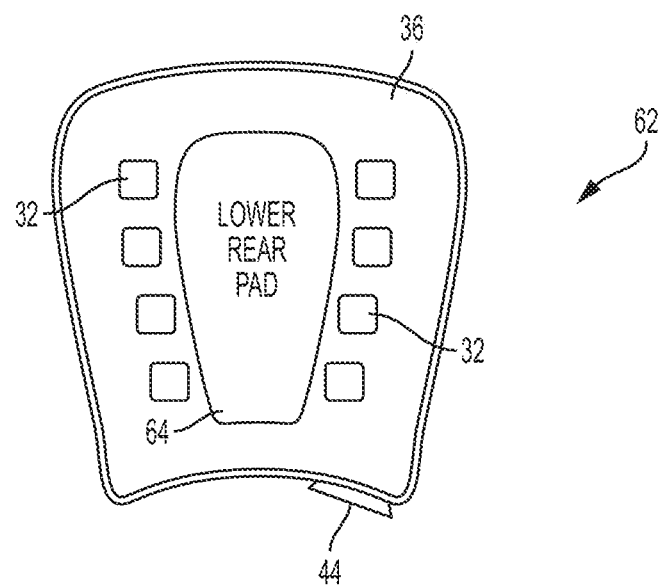

In other embodiments, depicted in FIGS. 13 and 14A-B the device 10 may include two units, applied to the body independently. In such embodiments, the TENS electrodes 32 may reside on a first unit and the motors 14 and remaining components on the second unit. The under-layer of the TENS 32 may include an enclosure 36, such as for example, a tube sock like carrier, a wrap, or alternative, with each electrode pad 34 loose, to be applied wherever the user desires. This would allow for the TENS electrodes to be aligned for optimal placement, such as for example to avoid the shin or any bony areas of the body. The TENS electrodes may be connected to a hub structure 44. The hub structure 44, enclosing the TENS connectors, may be enclosed inside a ribbon connector housed under the control unit 28. The hub structure 44 may also be tied to the first unit and the second unit by removing the ribbon connector housed under the control unit and attaching it to one or more of the first and second units. Either or both of the first unit 60 or the second unknit 62 may further incorporate cold or hot pads 64 throughout for additional muscle therapy. In various embodiments, the cold or hot pads 64 may be incorporated into the first unit 60 or second unit 62 by insertion into a sleeve or a recess located on the inside of the first unit 60 or the second unit 62. A portion (illustrated at the right of control unit 28) may be connected to the connector of another unit 60 or 62. In some embodiments, a ribbon connector may be removed to connect the units to one another. In the embodiment provided in FIGS. 14A-B, illustrates a two-piece design with upper unit 60 and lower unit 62, however a single piece design, as well as multi-piece designs are envisioned and incorporated herein. The single, or multi-piece designs may be chosen for ease of application to the muscle, as well as to promote and optimize therapeutic goals of the user. The second unit 62 of the device 10 contains the motors 14 and accompanying components for enacting compression, and the second unit 62 may be applied over the TENS electrodes 32 first layer 60.

In yet other embodiments, the device 10 may further include an exoskeleton type framework including, but not limited to, periscopic (longitudinally) and clamping down (circumferentially) movement capabilities. These components and features along with pivoting joints at various locations would assist in the application process and functionality of the device 10 with respect to encapsulating the end user's desired body part. The design aspect could involve a multi-piece approach, wherein the exoskeleton is separate in nature and applied independently or incorporated into the device 10 thereby applied concurrently with other components. Possible materials of the exoskeleton could include, for example, carbon fiber, plastic, resins, fibers, and/or metal.

Figure 15C:
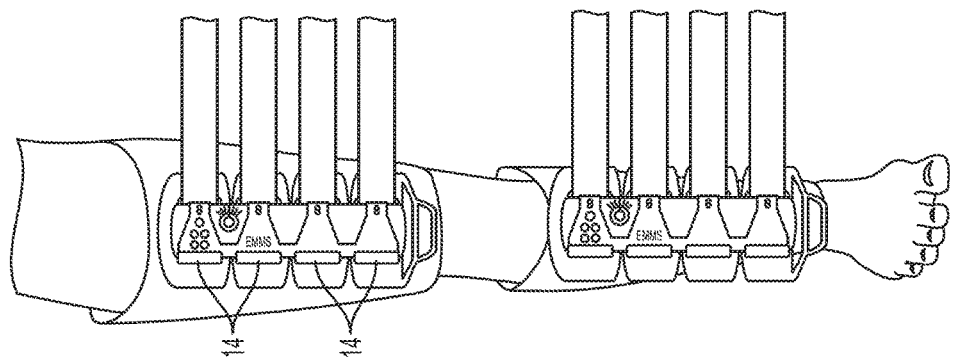
FIGS. 15A-15C illustrate application of an example embodiment of a muscle recovery device to a human leg.
Figure 15B:
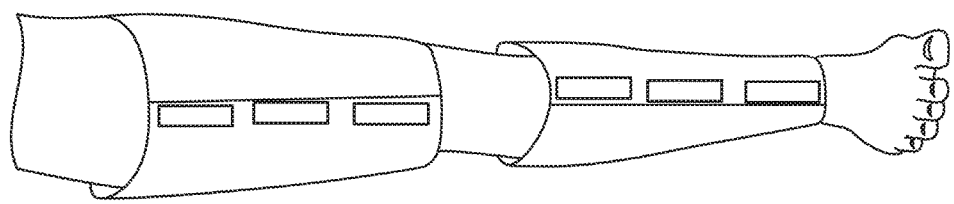
Figure 15A:
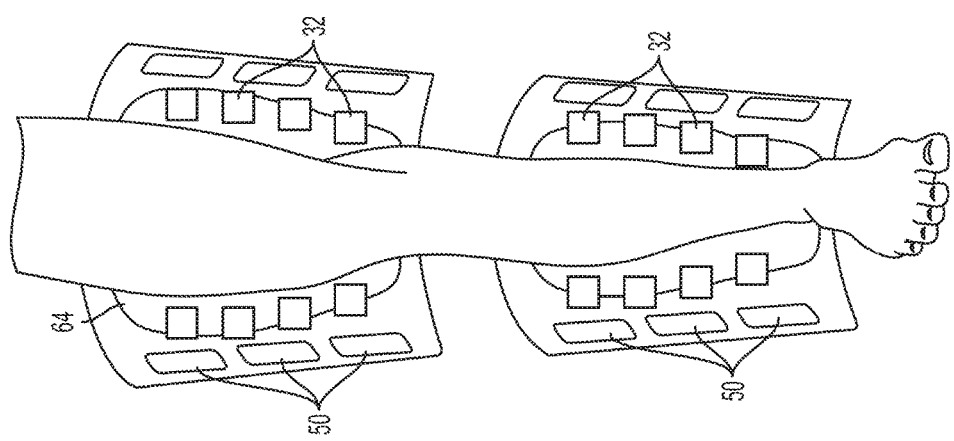

Application of an example embodiment of a muscle recovery device to a human leg is shown in FIGS. 15A-15C.

FIG. 15A illustrates a method of wrapping of the lower and upper leg with an example embodiment of the muscle recovery device 10, with the cooling/heating pads 64 positioned on the calf and the thigh muscles, and the locations of the optional TENS electrodes 32. In the embodiment of FIG. 15A, the device 10 includes fasteners 50 (which can be, for example, Velcro®) to adjust the size and snugness of the device 10 around the limb. Also, although not illustrated, the TENS electrodes 32 may be wired directly to the TENS main hub structure 44 incorporated into the device 10. From the TENS main hub structure 44, a ribbon cable may be connected to the control unit 28.

FIG. 15B illustrates an embodiment of the muscle recovery device 10 in which the full leg (thigh and calf) is enclosed prior to inclusion of the motor assembly. In other embodiments, the motor assembly may be included on the muscle recovery device 10 before application of the device onto the user's body part. The motor assembly may thus be separable from the padding underneath. In such embodiments, such as the example shown in FIG. 13, the motor assembly may be pre-connected to be coupled at the other end of the straps 12.

FIG. 15C illustrates the full assembly of the muscle recovery device 10 applied to the user's leg, including the motors 14. The embodiment illustrated in FIG. 15C includes four motors 14 included on a single enclosure. The single enclosure may include modular segments 26 as illustrated in FIG. 1, or such as for example are shown in FIG. 13, a main unit may contain all the components, drivers, and power to drive the device 10 within one enclosure. An auxiliary unit, which may communicate with the control unit 28 by a wired connection or wirelessly may also be connected separately to the main enclosure. This auxiliary unit may be replaced, or may incorporate a smartphone or other computing device, mobile or fixed.

Figure 16:
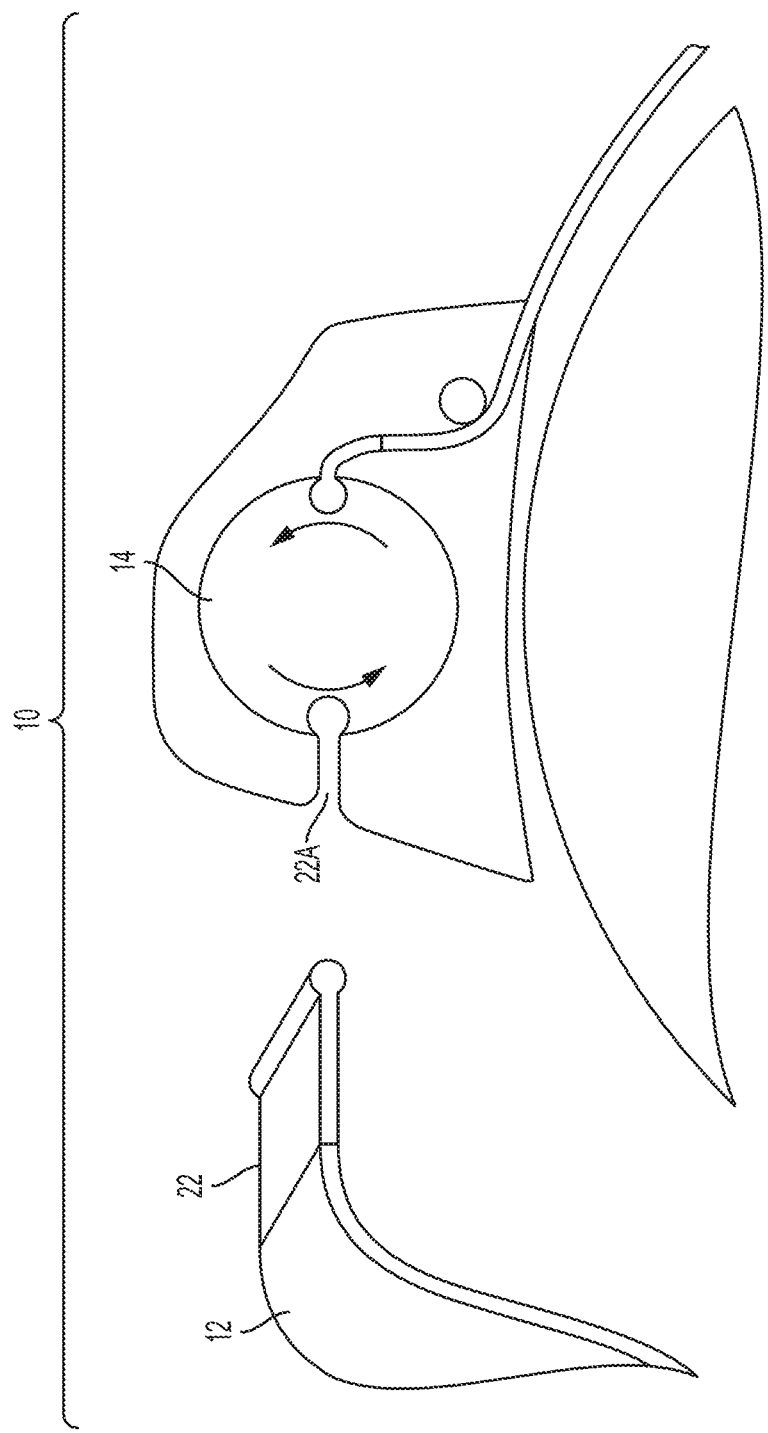
FIG. 16 illustrates connection between various components of an example embodiment of a muscle recovery device.

FIG. 16 illustrates connection between various components of an example embodiment of a muscle recovery device. In various embodiments, the motor barrel 18 includes a shape to accommodate connector 22. As illustrated in FIG. 16, a strap 12 with a connector 22 is inserted into motor unit 14 with a strap connector system 22A. The connector 22 may be a plastic connector in some examples. As the motor 14 rotates, it pulls and/or exerts tension on the strap 12, thereby tightening the strap 12 around the muscle onto which the device 10 is applied, all the while keeping the plastic connector 22 engaged. The user is then able to control the compression rate on the muscle by adjusting the rotational speed of the motor 14. The motor 14 may also be controlled to operate in pulsed mode, in alternate reverse and forward pulses, in sequenced pulses, and the like. The mechanical compression exerted onto the muscle is thus directly controlled by the motor 14.

Figure 17B:
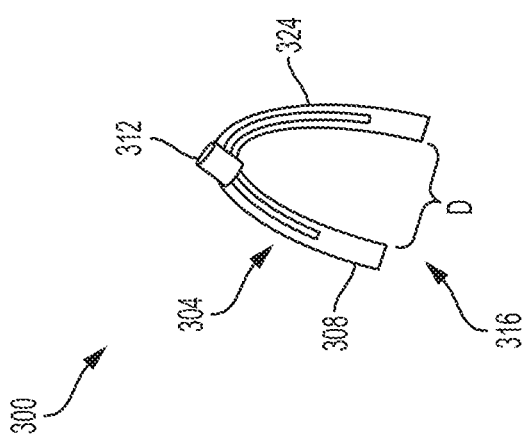
FIGS. 17A-17B depict another example embodiment of a muscle recovery apparatus.
Figure 17A:
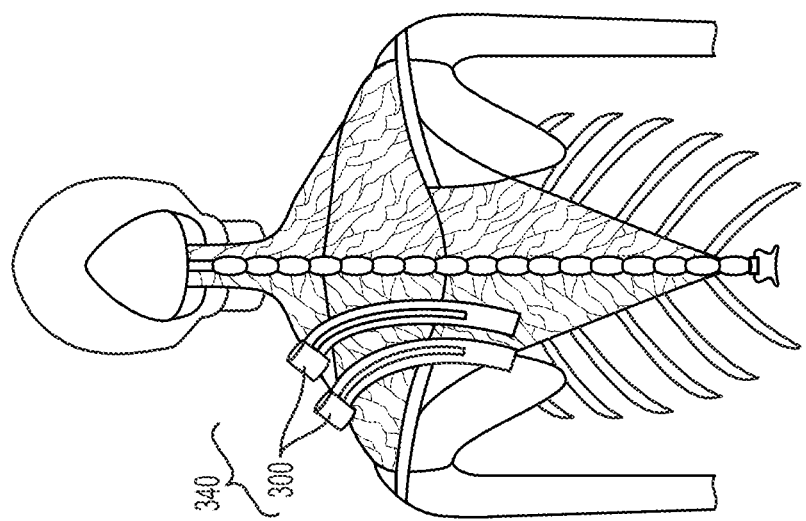

Another embodiment of a muscle recovery apparatus 300 is shown in FIGS. 17A and 17B. The recovery apparatus 300 can include an active compression device 304. The active compression of the apparatus 300 can be provided by a resilient base member 308. The active compression device 304 may include one or more motors 312 pulling apart or decreasing compression load of the base member 308. The base member 308 can be formed from any of a variety of materials fabricated with specific dimensions and resilience. In the illustrated embodiment, the base member 308 has an open end 316 configured to receive the shoulder of a user such that compression can be of the trapezius muscle. A distance D from one side of the base member 308 adjacent to the open end 316 to another side of the base member adjacent to the open end 316 is smaller than the anterior-posterior size of the user such that in the free state the base member 308 compresses the trapezius. It may also compress the pectoral muscle when applied or any other muscle/body part which the device may be applied. In such embodiments, the motors 312 are not used for applying the compression. With the motors 312 disengaged, the compression occurs upon the application of the device onto the desired area of the body through alteration of the baseline shape of the base member 308 depending on the characteristics of the material being used. Furthermore, the motors 312 help in removing compression loads when engaged, and therefore compression loads are returned upon the motors 312 being disengaged due to the resilient nature of the base member 308.

In such embodiments, the device or apparatus 300 may thus have an open-ended component in its nature. Such an open-ended configuration allows for application of the device or apparatus 300 on any muscle without necessarily encompassing the muscle completely. In the illustrated embodiment, the open ended apparatus 300 can include a load transfer member 324 that can interface between the output of the motor 312 and the base member 308. The load transfer member 324 is preferably a solid member capable of rapid if not instantaneous response. The load transfer member 324 in various embodiments is not reliant on inflation or fluid transfer to transfer a load. The load transfer member 324 can convey a load from the output of the motor 312 to open up the base member 308 to reduce the load on the tissue, e.g. on the muscle, more specifically in the illustrated case on one or both of the trapezius and the pectoral muscles. The open ended device 300 could also be configured to be applied to the patient in a free state with no load being applied to the tissue, e.g., to the muscle. In that case, the motor 312 can be configured to compress the base member 308, e.g., with the load transfer member 324 to compress the tissue, e.g., the muscle. Whether the motor 312 loads or unloads the base member 308 to compress the tissue, the apparatus 300 includes an active compression device. Although not specifically shown, the apparatus 300 can also include an electrical stimulation device, and/or a heating or cooling components. The apparatus 300 preferably includes the ability to rapidly load and unload the muscle in a direct compression manner by cycling tension or compression in the load transfer member 324.

FIG. 17B shows an apparatus 340 in which two recovery apparatuses 300 are applied to a muscle. The two recovery apparatuses 300 may include any or all of the controllers, couplers, connectors described in conjunction with other embodiments herein. The apparatus 340 can be similar to those described elsewhere herein in which the motors 312 can be actuated in a predefined sequence. The sequence can include synchronized rapid pulsing of the compression in a first motor 312 disposed over the clavicle adjacent to the head and pulsing a second motor 312 of a second apparatus 300 disposed between the first apparatus and the arm. In another embodiment first and second motors 312 can be counter-pulsed such that compression on a device 300 closer to the head occurs when relaxation of a device closer to the arm occurs. The rate (or magnitude) of pulsing could also be different for different regions of the muscle. For example, higher frequency pulsation could be provided in the trapezius or pectoral muscle adjacent to the arm than adjacent to the neck in one approach. In another approach, lower frequency pulsation could be provided in the trapezius or pectoral muscle adjacent to the arm than adjacent to the neck. As another example, higher magnitude pulsation could be provided in the trapezius or pectoral muscle adjacent to the arm than adjacent to the neck in one approach. Or, lower magnitude pulsation could be provided in the trapezius or pectoral muscle adjacent to the neck than adjacent to the arm. Because the motors 312 (and other motors described herein) can be precisely controlled and their movement can be rapidly deployed to the tissue through the load transfer member 324 many more cycles per short treatment period (e.g., a matter of minutes) can be provided as compared with balloons or other modes of transferring fluctuating pressure.

The design of the device 10 and its application may further incorporate leaving various segments of the body (such as, for example, the knee) open and exposed for a trainer, or physician to work on, while portions of the rest of the body are being stimulated by the device 10. The device 10 may also allow for mobility of user while the device 10 is active. In addition, a cloth undercarriage with removable components may allow for the user to periodically wash the cloth undercarriage. Furthermore, the device 10 may be able to be used before, during or after physical activity, as a warm-up, cool-down, or warmth maintenance tool.

Contemplated application for the device 10 includes: aid in injury recovery, decrease in muscle atrophy, pain management, temporary alteration of blood pressure, mental relaxation, muscle recovery, muscle rejuvenation, and entertainment reasons.

Further details of the mechanical compression and electrical stimulation are described below. Although, the description focuses on the human leg and muscles germane to the human leg, additional embodiments may be applied to any active muscle in the human body, as well as passive and active muscles in any animal. Accordingly, the present invention is intended to cover any and all application of the method, system and device 10 for all muscles.

Mechanical Component:

Multiple straps 12, exemplified as segments 26, may be aligned around the circumference of a leg from foot to hip to provide a sequential compression. Each strap 12 is attached to an individually activated motor 14, controlled by a control unit 28. The straps 12 are wound around the motor 14 so that engaging the motor 14 pulls the strap 12, compressing the leg in effect. By activating each motor 14 individually, the compression can be provided in any desired manner. A sequential activation would force interstitial fluid to flow through the leg and encourage the cycling of fresh blood.

The straps 12 could include one or more of a variety of materials including but not limited to: fabrics, plastics, metals, carbon fiber, resins, or fibers with varying levels of rigidity. Additionally, these straps or compression elements can be housed inside or apply force onto the same variety of materials with varying levels of rigidity.

The particular sequence in which the motors 14 may be engaged in can be varied to provide a different effect. A particular sequence that may be most conducive to encouraging blood cycling may be compressing and holding a strap 12 before activating the next above it, and releasing the strap when the strap 12 two above it has been engaged. In the engaging process the motors 14 can provide a pulsed compression to increase efficacy, compared to a linear compression.

In order to provide the force necessary without harming the motors 14, an intelligent feedback system can be implemented electronically to hold the motor 14 position once a certain current draw threshold has been reached.

The straps 12 may include a breathable fabric which can be detached from the motor 14 assembly to be washed/rinsed, or swapped with different sized straps 12 while keeping the same motor 14 assembly. In various other embodiments, the motors 14 used for applying compression may be controlled by varying direction, torque, speed, position, and braking via regenerative method or coasting.

Electrical Component:

Electrical stimulation is applied directly to the target muscle in synchronization with the mechanical compression to effect deeper muscles. The electrical stimulation may be provided, for example, by a high voltage, low current exponentially decaying pulse. The pulse may be initiated in both positive and negative directions. The effectiveness of the pulse will be dependent on the applied voltage (for example, about 150v) with the current limited for user safety. The pulse amplitude may be user controlled to a desired level of muscle activation. Other controllable factors include the frequency and the duration of the pulse. The particular waveform does not have to be limited to exponential decay, but may also be a bimodal square, saw tooth, or sinusoidal wave, among others.

The pads 34 used to transmit the electrical pulse may include a conductive pad or fabric. The placement may include two pads 34 placed at the extremes of the unit to activate the entire muscle as a whole. Or the placement can be broken down into segments similar to the mechanical compression, requiring additional pads 34. This allows for the individual and sequential electrical activation of muscle groups. The relative synchronizing of electrical stimulus with compression stimulation is used to enhance the fluid flow stimulation significantly. Each segment 26 may further be broken into various zones for finer control.

Advantage(s) of Combining Multiple Modalities

The combined electrical and mechanical stimuli in synchronization with one another provides an improved recovery effect. First, individually the mechanical and electrical effects will be separated into numerous zones spread throughout the leg in a graduated fashion originating from the most distal point in relation to the heart and moving towards the heart. As a result of increasing the number of zone specific areas to affect, both concentration of effects and decreasing recovery times can be achieved through higher frequency rates of mechanical and electrical processes. Second, by the means of synergistic effect, the overall time associated with aspects of muscle recovery are significantly reduced. This synergistic effect results by either the electrical effect preceding the mechanical, the mechanical preceding the electrical, or the simultaneous effects of both in each isolated specific zone. Third, the zones may be coordinated in sequence to increase the natural effect and efficiency of the lymphatic system in aiding muscle recovery. Fourth, the variability and customizability of all the zones (and patterns that potentially could be taken) by the user would optimize the time for recovery. Finally, the combination of electrical and mechanical stimuli allows for much more aggressive treatment of the muscles due to the balancing and counteracting effects of the two treatment methods, simultaneously. In addition, time would be reduced by eliminating the unnecessary location change to different muscle groups of product interfaces by the user. One example of such location change may involve the application of TENS electrodes.

In operation, the device 10 may activate individual compressive segments 26 in multiple and various sequences controllable by a user, and also including a default pattern where each segment 26 activates following its adjacent segment 26 to simulate a directional effleurage. The variations in sequence are not limited to any predefined pattern, nor does the sequence need to follow adjacent segments 26. A sequence which implements or mimics a rhythmic pattern which may be derived from a song or other source of music or rhythm may be implemented with the device 10. This might include external auditory (direct or ambient) input of music, speech, or other patterns of data in order to direct and synch with the device's 10 outputs and sequencing of both mechanical compression and TENS electrodes. In addition, different segments 26 of the device 10 may act as different notes, or a pulsing activation of the motors 14 can be made to simulate a note so that the device 10 as a whole can emulate a melody.

The device 10, through control of the motors 14, or with incorporation of additional components, may produce varying levels of vibration along with the compression element achieved on zones individually and synergistically synchronized with each other. Vibration can be utilized on varying levels of predetermined compressed tissues accomplished with or without initial motor engagement. The vibration may be utilized for muscle recovery and/or preparing muscles for compression stimuli and/or electric stimulation. For example, vibration may be utilized to disguise or obscure discomfort or pain caused by higher levels of compression or electric stimulation. Vibration may be accomplished by using solenoids, which may also be used for compression stimuli. In one embodiment, the motors may be used to fit the device 10 on the user's muscle, and provide a custom fit. The individual solenoids may then be used for vibration and/or for compression stimuli. In one embodiment, once straps are initially tightened down by the motors, the entire housing turns into a solenoid with forces being applied relative to the housing's attached base.

The device 10 disclosed herein may be powered via internal batteries to allow for portability, or by other conventional AC or DC power sources. The batteries may be removable or non-removable, rechargeable or single use. Rechargeable batteries may be charged while within the device 10 or removed to be charged separately.

In various embodiments, the device 10 may be configured for use and/or communication with additional electronic devices, including, smartphones, PDA, computers, and the like. Communication may include the use of wireless protocols such as, but not limited to, Bluetooth, Wi-Fi, or NFC to connect to an electronic device 10. The device 10 may also use wired communication such as, but not limited to, USB, serial, or parallel communication. One purpose for such connection would be to control internal parameters or settings by user or technician or by algorithms to manipulate the device 10 in a desired manner.

Temperature Component:

The device 10's capabilities individually and/or in combination essentially create an external pump. Whereas the heart is an internal pump to drive and push fluid away from the center of the body towards the extremities, the device 10 acts as an auxiliary external pump aiding fluid from the extremities back towards the center mass of the body. Therefore, the application of a hot or cold temperature controlled sock (in addition to the other temperature applications previously mentioned—hot or cold wrap material housing TENS electrodes) can further aid in driving local and core body temperatures back to the optimal baseline levels. This would decrease the body's energy consumption demands at certain times and assist in overall recovery objectives.

Mechanical Design:

The mechanical design of the device 10 may allow for ultimate flexibility and customizability. The individual components or systems may be easily removed and swapped. The motor 14 may be mounted in a casing, which may readily snap into the motor 14 mount to work reliably, yet allow for the user to easily remove and replace the motor 14, whether for repair, upgrade, cleaning, or other reason. The motor 14 mount attachment to the undercarriage may also be easily removable to allow for the entire mount with motor 14 inside to be removed. This may be for, but is not limited to, separating sensitive components so that the undercarriage may be washed. Each segment 26 itself may be removable and replaceable without replacing the entire unit. This may be possible due to the separate segments 26 that fasten together via zipper or other mechanical fasteners. This may allow for adding or removing of extreme zones to allow for the unit to fit onto longer or shorter bodies, or with the swapping of segments 26 with different shaped or proposed units whether to gain a better fit, apply an upgraded segment 26, or to replace a segment 26 for any reason desired.

The control unit 28 containing all the components, drivers, and power to drive the device 10 may be contained within an enclosure that is wired to the device 10, or it may be integrated directly into the device 10. An auxiliary unit for user input may be available for convenient access to settings, which may communicate settings to the control unit 28 by a wired connection or wirelessly. This auxiliary unit may be replaced, or may incorporate a smartphone or other computing device, mobile or fixed.

The TENS 32 electrodes may be mechanically attached to the undercarriage through a variety of fasteners, including but not limited to hook and loop, Dual-Lock, snaps, or directly attached to the undercarriage. A removable electrode allows for easy replacement or upgrade.

The electrical connection to the TENS electrodes may be through a direct connection where the leads are wired together, there may be a harness or connector to allow for easy removal, the connection may be through conductive snaps so that both the mechanical and electrical attachment occur through one point. The electrodes may not be mechanically attached to the undercarriage in which case the electrical connection may be through the contact of conductive backing on the electrodes coupled to a conductive pad on the undercarriage, this may be through, but is not limited to, a conductive fabric, or metal weave. Additionally, the electrodes could be contained in their own individual removable housings with wireless communication features. These housings could contain their own variety of independent power supply or shared with the associated power supply of the areas compression mechanism. The opening of these housings might be detachable as in thin plastic strips, hard covers, hinged doors, sliding caps, or sliding doors.

Mechanical Compression Conversion/Strap Pull:

Multiple modalities may be utilized to convert the rotational force exerted by the motor 14 to a linear motion to pull a circumferentially wrapped strap 12 to provide compression. For example, a cylindrical barrel 18 will enable the strap 12 to wrap around it as the motor 14 rotates the cylindrical barrel 18. This provides a constant torque regardless of angular position of the barrel 18. Another approach may be to use an oblong barrel 18 with an oval shaped profile, instead of the circle profile of a cylindrical barrel. An oblong barrel 18 produces a different torque, with the speed ratio depending on the angular position of the barrel 18. This can be used to apply a fast, low torque pull followed by a slower, but higher torque pull toward the end to provide more compression. The profile of this oblong barrel 18 may be adjusted to suit the needs of the application, it need not be oval, and can be spiral or other shape with a varying radius dependent on the angle.

A crankshaft like approach can be utilized to allow for as few as one motor 14 to drive multiple segments 26. The crankpins would transfer the rotational energy of the motor 14 to a linear pull onto the strap 12 of each segment 26. Similar to this, a camshaft can be used where the cams can be changed as necessary to provide a varying or customizable compression.

Another method of using the rotational energy of a motor 14 to provide linear pull may employ a worm gear to pull a carriage attached to the strap 12 effectively pulling the strap 12 and providing compression to the leg.

More methods of creating compression may be achieved through the usage of cylindrically weaving fabrics or other materials in specific patterns which would compress circumferentially when force is applied on its linear or longitudinal axis. This method is similar to the Chinese finger trap concept, for example.

The motors 14 may be stacked side by side and staggered at a half offset from one another to provide a denser stack and a more continuous flow of compression. This would be in contrast to stacking the motors 14 end to end, with one per horizontal section, as previously proposed.

Figure 7:
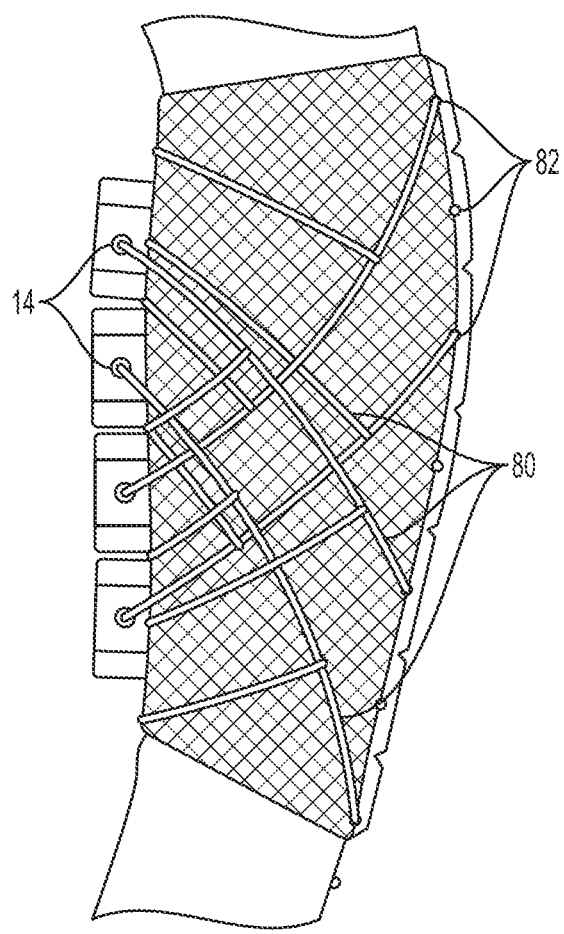
FIG. 7 illustrates a side perspective view of an example embodiment.
Figure 8:
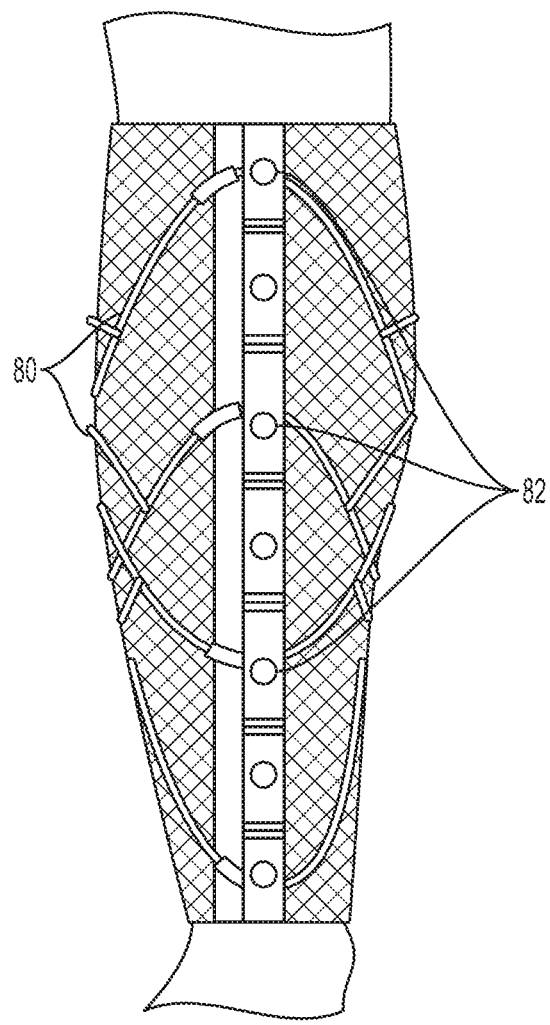
FIG. 8 provides a front perspective view of an example embodiment.
Figure 9:
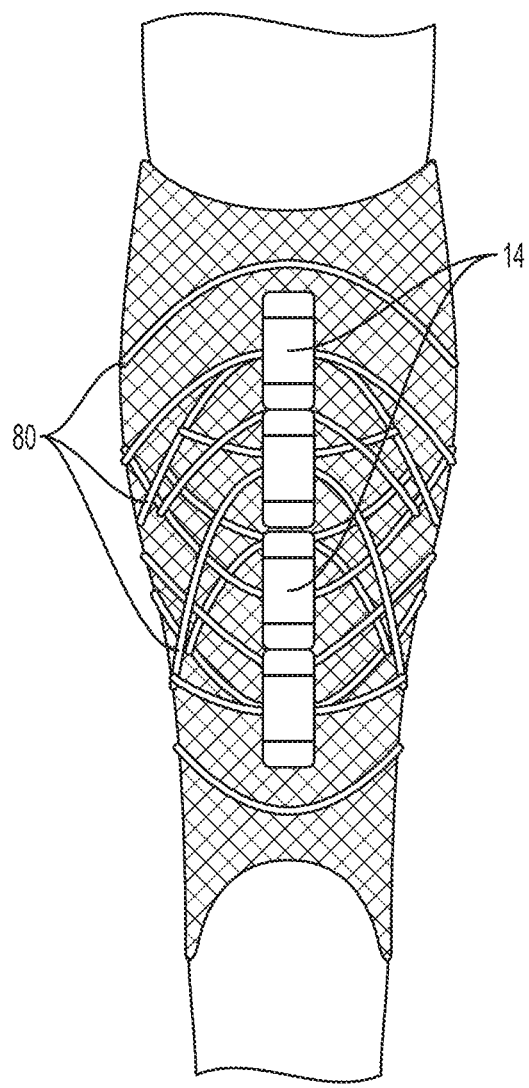
FIG. 9 depicts a rear perspective view of an example embodiment.

A further embodiment for compression, depicted in FIGS. 7 through 9, may use a cord or cable 80 instead of a strap 12 to be pulled and provide compression. A cord 80 may then be wound around a pulley 82 to give a mechanical advantage. Further, the cord 80 may be wrapped around multiple pulleys 82 to give an even greater advantage. The pulleys 82 may be stacked vertically so that an uneven compression is provided, where the pulley 82 closest to the motor 14 drawing the cord 80 compresses first the adjacent pulleys 82 follow. This embodiment may be further refined to allow a single motor 14 to provide continuous compression from one end of the device 10 to the other. Furthermore, additional motors 14 may be incorporated at varying points along the pathways of the pulleys 82 to gain increased power and control of the compression sequence or wave.

Figure 10:
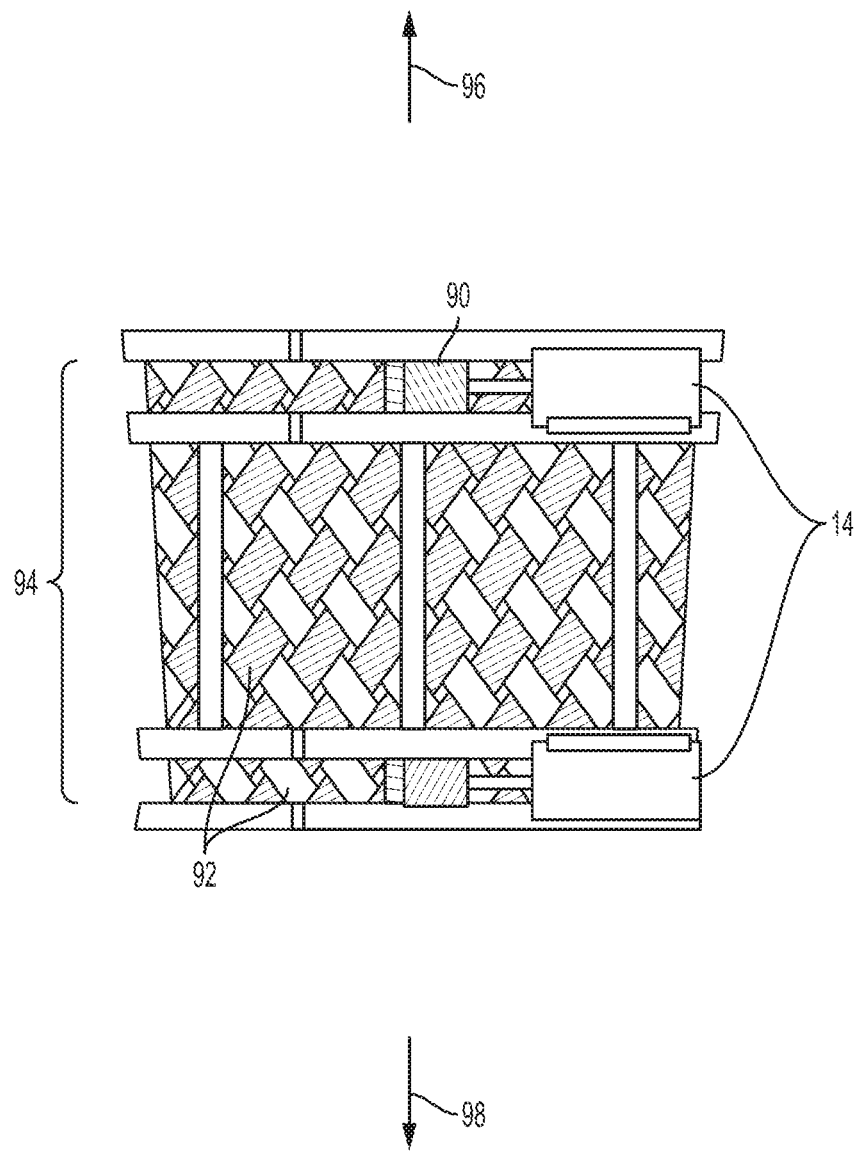
FIG. 10 illustrates a side perspective view of an example embodiment.
Figure 11:
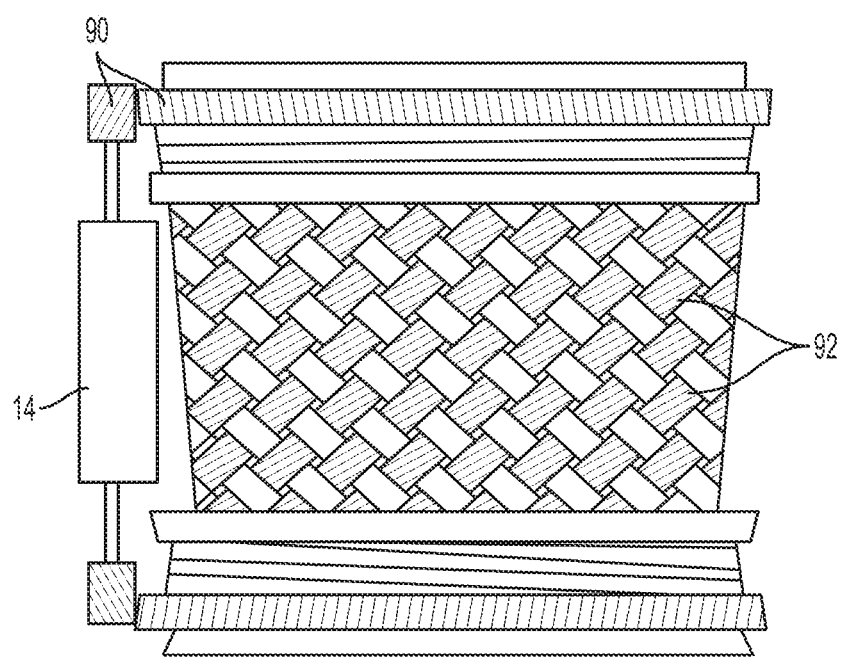
FIG. 11 depicts a side perspective view of an example embodiment.
Figure 12:
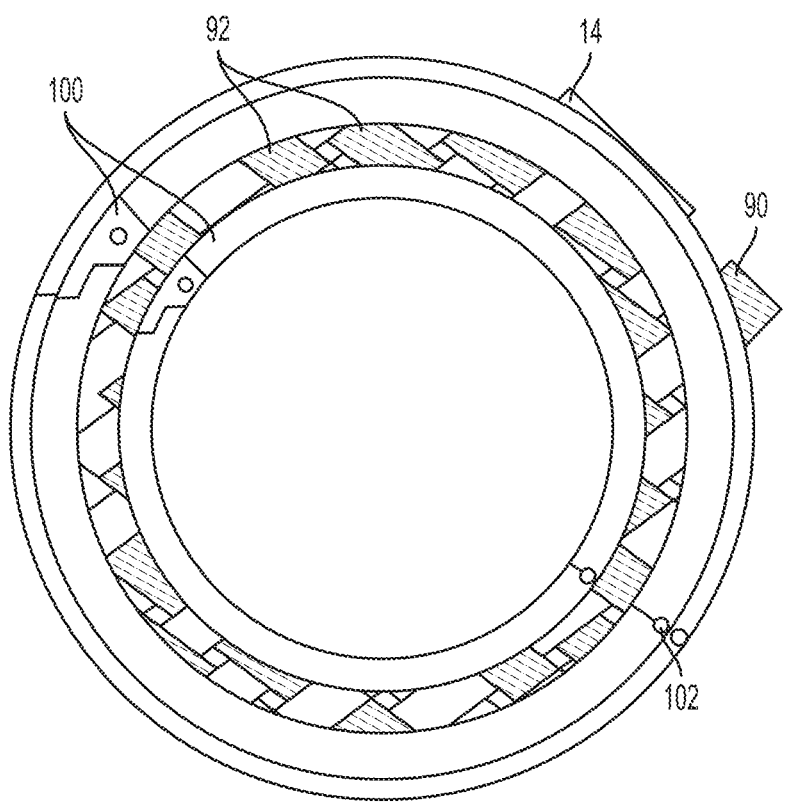
FIG. 12 depicts a top perspective view of an example embodiment.

A further embodiment, depicted in FIGS. 10 through 12, includes motors 14 pushing and pulling multiple cords 92 incorporated onto a single piece or multiple piece soft, semisoft, or rigid muscle enclosure wherein the cords 92 are attached in a weave configuration 94 exerting force on each other. The motor 14 may act upon a screw drive 90 to alter the overall shape (depicted by arrows up 96 and down 98) of the weave 94 to conform to the user's body/appendage shape. The device 10 may be applied and removed from a user's muscle incorporating a latch 100 and hinge 102 system which allows one part of the device 10 to pivot about a second part of the device 10.

A further embodiment for compression can be achieved in zones through the use of a shape-memory alloy (NiTi—nickel titanium being one example).

A further embodiment for compression can be achieved in zones through the use of pneumatic mechanisms.

Control Program:

The software and hardware designed to control the device 10 may manage each segment 26 individually and independently of one another, both for the TENS electrodes and mechanical compression. The control program may work by assigning a certain ON time for each segment 26 relative to an internal clock, and an OFF time relative to the ON time. This way, the desired state of each motor 14 or TENS electrode can be continuously checked relative to the internal clock as to not block the computation of the microcontroller.

The controls also allow for multiple devices 10 either on a single user or multiple users to be connected locally or remotely thereby allowing for shared/replicated functions and patterns of the device 10 concurrently or delayed. The capabilities and controls of the device 10 enable an environment for a "shared recovery experience" or shared entertainment among various users.

Hardware:

The motors 14 may be controlled using a low side Field-Effect Transistor (FET) to provide an ON-OFF function. The control can be enhanced by using a discrete FET H-bridge configuration for each motor 14 to provide a forward and reverse function. Furthermore, a discrete or integrated driver may be used to run the motors 14, including for example the STMicroelectronics L298, or Freescale MC33926. Such drivers may also be able to provide current draw metrics for more intelligent activation of the motors 14, and current regulated control of the motors 14. Current draw readings may also be obtained via a current sense resistor.

The high voltage pulse for the TENS electrodes may be generated using a boost, flyback, or single-ended primary-inductor converter (SEPIC) circuit. The voltage may be controlled to the desired user threshold. The circuit may be voltage controlled and current limiting as to mitigate any undesired electrocution. The energy of the boost circuit may be stored in one or more capacitors so that one may be discharged immediately following the other to provide an even and opposite biphasic pulse. The TENS electrodes placed on the user are electrically isolated from one another, and the TENS pulse may be sent to any electrode pair, not limited to their respective horizontal zones. While normally, the electrode pair corresponding to the currently activated motor 14 will fire, making for a localized muscle stimulation, any pair can be made to fire so that a muscle spanning the entire length of the device 10 may be activated.

The type of TENS electrode used may include an adhesive gel electrode, non-adhesive carbon electrode, or conductive fabric, among others.

The control unit may contain visual and/or audible indicators, to provide the user with feedback regarding the current state of the device 10. The indicators may include LED's and bar graphs to display compression strength, rate of activation delay, or TENS voltage, for example. The indicators can also be realized through a LCD screen, or through visual or audible communication to the user's computer or smartphone.

Modalities:

The unit has the capacity to deliver localized compression and electrical muscle stimulation to enhance recovery. The device 10 may also contain ultrasound and ultrasonic modalities. The device 10 may also incorporate thermal modalities, including cooling and heating, which may be localized to the zones unique to this device 10. Heating may be provided through, for example, Peltier heat pumps, resistive heaters, or hot packs; cooling may be provided through, for example, Peltier heat pumps, or cool packs inserted into the device 10. The thermal modalities may utilize copper bands integrated within the unit to disperse or absorb heat. Additionally, light or laser source therapy may be incorporated as another modality. Ultimately, these modalities are combined in a synergistic method to produce a customizable and pattern-able wearable device 10.

Intelligent Control:

The device 10 may employ sensors to gather information including device 10 performance and user biometrics. The information gathered may be used for logging, recovery tracking, or the device 10 may employ an intelligent algorithm to maximize its effectiveness without any user intervention. Sensors may include, but are not limited to, measurements of heart rate, heart rate variance, blood flow, galvanic skin conductance, local tissue temperature, core body temperature, blood pressure, oxygen saturation levels in blood, volumetric measurements of tissue edema, and also chemical sensors to read into sweat conditions and provide the user with useful feedback. These and other variety of sensors may be placed at multiple points on the human body, including at both ends of the device 10. The gathered information may be used to optimize the user's desire from the device 10, be it injury, or fatigue recovery, or warming up, cooling down, or pain management, or muscle regeneration, or edema prevention. The stress the device 10 is causing may be quantifiable and regulated internally by the device 10 itself to prevent overworking the body, providing a sub-maximal recovery, or desired efficacy. The pressure exerted by the device 10 may be sensed and incorporated in the recovery algorithm or just logged and displayed for the user.

Additional Technology Application:

The device 10 may further be modified to incorporate TENS electrodes into a foam or plastic type roller used to treat various tendon and muscle needs. In this aspect the mechanical compression element would be controlled and manipulated through the user's interaction with engaging variable amounts of their body mass with pre-existing gravitational forces found commonly in most geographic locations. The TENS electrodes are also controllable based on various patterns and sizes of electrode pads designed onto the roller which the user would dictate the level of engagement with locations, sizes, and configurations of previously said pads. The control points of the device 10 would include, but not be limited to, roller material and density, rate at which the roller is physically being accelerated by the user, amount of mass applied by the user, tens controls/modes, and electrode pad types, sizes, numbers, configurations, type of ointment used with. Additionally, the roller could have an incorporated chamber to house a removable heating or cooling element to be determined by the user's desired objectives.

The device's capabilities by means of software incorporation allow customizable control of electrical stimulation and mechanical compression. The variable of temperature control is accomplished through inclusion of hot, cold, or neutral materials. The TENS electrodes' components variables include: number of pads, location of pads, size of pads, interferential capability, wave form/shape, wave polarity, voltage/current levels, rate of waves, overall rate modulation/variability, wave width, tens offset compared to compression sequence, and possibly more. The mechanical compression variables include: number of zones, location of zones, compression strength, vibration (including frequency, strength, duration, modulation/variability), compression rate, compression hold time, and possibly more. Electric motors and solenoids can be configured for the present application to provide mechanical pressure modulation, e.g., mechanical compression, at a frequency between about 0 and about 1 KHz. Mechanical pressure modulation, e.g., compression, for the muscle recovery device here may be provided at a rate up to 200 Hz. Mechanical pressure modulation, e.g., compression, for the muscle recovery device here may be provided at a rate of about 10 Hz to about 150 Hz. Mechanical pressure modulation, e.g., compression, for the muscle recovery device here may be provided at a rate of up to about 100 Hz in some embodiments. Such compression rates can provide sufficient or full flushing of a portion of or an entire leg of a user (which may include application of the device on eight or more zones, in some embodiments) in a fraction of a second. Together these customizable components manipulated by various inputs synergistically create the desired experience. The various inputs could include: preset algorithms, synced auditory input, synced visual input, synced motions (via accelerometers and gyroscopes), human driven external controllers, and possibly more.

The following example sequence of elements in the device's experience enables the conservation of low energy levels observed in the body's tissues to be directed towards recovery through maximum muscle/tissue recruitment:
 1. initial compression of device application;
 2. altered temperature associated with materials of device;
 3. application of TENS;

4. increased static mechanical compression;
5. massage/sequential synchronization of TENS and mechanical compression;
6. vibration modes; and
7. incorporation of musical or other psychological integrations of recovery elements.

As used herein, the relative terms "proximal", "distal", "anterior", "posterior", "medial", and "lateral" shall be defined from the perspective of the leg or other extremity. Thus, distal refers the direction of the leg or extremity toward the free end thereof and proximal refers to the direction of the leg or extremity toward the torso. Anterior refers to forward part of the leg or extremity, e.g., in the case of the leg the side where the patella is located. Posterior refers to the rearward part of the leg or extremity, opposite the anterior part. Medial refers to the side of the leg or extremity facing toward to the sagittal plane. Lateral refers to the side of the leg or extremity facing away from the sagittal plane.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

The terms "approximately," "about," and "substantially" as used herein represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, 0.1 degree, or otherwise.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Although these inventions have been disclosed in the context of certain preferred embodiments and examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Further, the actions of the disclosed processes and methods may be modified in any manner, including by reordering actions and/or inserting additional actions and/or deleting actions. Thus, it is intended that the scope of at least some of the present inventions herein disclosed should not be limited by the particular disclosed embodiments described above. The limitations in the claims are to be interpreted broadly based on the language employed in the claims and not limited to the examples described in the present specification or during the prosecution of the application, which examples are to be construed as non-exclusive.

What is claimed is:

1. A muscle recovery apparatus comprising:
a compression device having a strap attached to a motor wherein rotating the motor causes the strap to deliver active compression and decompression of a muscle of a user, wherein one compression and decompression cycle is performed at least once every 3 seconds;
an electrical stimulation device having at least two electrodes adapted to be in contact with the user wherein the electrical stimulation device is configured to deliver electrical current for stimulation of the muscle of the user during use;
a controller in communication with the compression device and the electrical stimulation device to control a rate of active compression and decompression and synchronize the compression device with the electrical stimulation device to operate simultaneously, wherein electrical stimulation occurs only during active compression; and
a power supply in communication with the compression device and the electrical stimulation device.

2. The apparatus of claim 1, wherein the muscle recovery apparatus is configured to attach and communicate with one or more additional muscle recovery apparatuses.

3. The apparatus of claim 2, wherein at least one of the one or more additional muscle recovery apparatuses is pivotally attached to the muscle recovery apparatus to allow for relative movement of the muscle recovery apparatus and the at least one of the one or more additional muscle recovery apparatuses in at least one axis.

4. The apparatus of claim 1, wherein compression of at least a portion of the muscle by the compression device and the stimulation of the muscle by the electrical stimulation device occur sequentially.

5. The apparatus of claim 1, further comprising a thermal modality configured to deliver at least one of heat and cold to the muscle of the user.

6. The apparatus of claim 1, further comprising a vibrator.

7. The apparatus of claim 1, wherein the compression device further comprises a fastener to removably secure the muscle recovery apparatus.

8. The apparatus of claim 1, wherein the controller is configured to adjustably and independently control delivery of the active compression and the decompression, and the electrical stimulation.

9. The apparatus of claim 8, wherein control of the active compression and decompression and the electrical stimulation by the controller is a rhythmic control of the active compression and decompression and electrical stimulation.

10. The apparatus of claim 1, wherein the power supply is at least one of: a battery, an AC supply, a DC supply, and a photovoltaic supply.

11. The apparatus of claim 1, further comprising
at least one sensor for monitoring biometrics of the user.

12. The apparatus of claim 1, wherein the compression device is configured to facilitate blood flow and the electrical stimulation device is configured to electrically stimulate the muscle of a user.

13. The apparatus of claim 1, wherein the controller is configured to control the rate of active compression and decompression, and the electrical stimulation in response to an external data pattern.

14. A muscle recovery apparatus comprising:
a removably coupled compression device having a strap attached to a motor wherein rotating the motor causes the strap to deliver active compression and decompression of a muscle of a user, wherein one compression and decompression cycle is performed at least every 3 seconds;
an electrical stimulation device having at least two electrodes adapted to be in contact with the user wherein the electrical stimulation device is configured to deliver electrical current for stimulation of the muscle of the user during use according to a controlled pattern;
a controller in communication with the compression device and the electrical stimulation device to control a rate of active compression and decompression and synchronize the compression device with the electrical stimulation device to operate simultaneously, wherein electrical stimulation occurs only during active compression; and
a power supply in communication with the compression device and the electrical stimulation device.

15. The apparatus of claim 14, wherein the electrical stimulation device is adapted to be removably coupled to the user by a fastener.

16. The apparatus of claim 15, wherein the fastener for affixing the electrical stimulation device to the user includes at least one of:
a strap, resilient fabric, mesh, and wires.

17. The apparatus of claim 14, wherein the compression device is removably coupled atop the electrical stimulation device by a fastener.

18. The apparatus of claim 17, wherein the fastener for affixing the compression device to the user includes at least one of:
a strap, resilient fabric, mesh, and wires.

19. The apparatus of claim 14, wherein the muscle recovery apparatus is configured to attach and communicate with one or more additional muscle recovery apparatuses.

20. The apparatus of claim 14, wherein the controller is configured to control the rate of active compression and decompression, and the electrical stimulation in response to an external data pattern.

21. A method for treating a muscle comprising:
positioning a compression device having a strap attached to a motor wherein rotating the motor causes the strap to deliver active compression and decompression of a muscle of a user;
positioning an electrical stimulation device having at least two electrodes adapted to be in contact with the user;
activating the electrical stimulation device to electrically stimulate the muscle by delivering an electrical current for stimulation;
activating the compression device to mechanically compress and decompress the muscle of the user at a rate of more than one compression and release cycle every 3 seconds; and
controlling the rate of active compression and decompression and synchronizing the compression device with the electrical stimulation device to operate simultaneously, wherein electrical stimulation occurs only during active compression.

22. The method of claim 21, further comprising independently activating the electrical stimulation device and the compression device to adjust the electrical stimulation and mechanical compression and decompression to a desired specification.

23. The method of claim 21, further comprising activating the electrical stimulation device and the activation of the compression device in a sequential manner.

24. The method of claim 21, further comprising non-sequentially activating the electrical stimulation device and the compression device.

25. The method of claim 21, wherein one or more of the compression device and the electrical stimulation device is configured to engage and communicate with one or more additional compression devices and electrical stimulation devices.

26. The method of claim 21, further comprising the step of controlling the rate of active compression and decompression, and the electrical stimulation in response to an external data pattern.

* * * * *